US009587237B2

(12) United States Patent
Hyde et al.

(10) Patent No.: US 9,587,237 B2

(45) **Date of Patent: *Mar. 7, 2017**

(54) COMPOSITIONS, METHODS, AND COMPUTER SYSTEMS RELATED TO MAKING AND ADMINISTERING MODIFIED T CELLS

(71) Applicant: Elwha LLC, Bellevue, WA (US)

(72) Inventors: Roderick A. Hyde, Redmond, WA (US); Wayne R. Kindsvogel, Seattle, WA (US); Gary L. McKnight, Bothell, WA (US)

(73) Assignee: Elwha LLC, Bellevue, WA (US)

( * ) Notice: Subject to any disclaimer, the term of this patent is extended or adjusted under 35 U.S.C. 154(b) by 456 days.

This patent is subject to a terminal disclaimer.

(21) Appl. No.: 13/804,224

(22) Filed: Mar. 14, 2013

(65) Prior Publication Data

US 2014/0271579 A1 Sep. 18, 2014

(51) Int. Cl.
*C12N 15/10* (2006.01)

(52) U.S. Cl.
CPC ................................ *C12N 15/1037* (2013.01)

(58) Field of Classification Search
CPC ...... A61K 2035/124; A61K 2039/6006; G06F 19/10; G06F 19/18; G06F 19/22; G06F 19/24; G06F 19/3487
See application file for complete search history.

(56) References Cited

U.S. PATENT DOCUMENTS 5,202,238 A 4/1993 Fell, Jr. et al.
5,601,819 A 2/1997 Wong et al.
5,928,914 A 7/1999 Leboulch et al.
6,103,521 A 8/2000 Capon et al.
6,130,364 A 10/2000 Jakobovits et al.
6,410,319 B1 6/2002 Raubitschek et al.
7,197,400 B2 3/2007 Liu et al.
7,354,762 B2 4/2008 Jensen
2003/0082719 A1 5/2003 Schumacher et al.
2005/0026199 A1 2/2005 Shaw
2005/0129671 A1 6/2005 Cooper et al.
2006/0018878 A1 1/2006 Cooper et al.
2006/0067920 A1 3/2006 Jensen
2006/0074566 A1 4/2006 Najarian
2006/0240482 A1 10/2006 Kwok et al.
2007/0036773 A1 2/2007 Cooper et al.
2007/0166327 A1 7/2007 Cooper et al.
2009/0191172 A1 7/2009 Cooper et al.
2010/0009863 A1 1/2010 Himmler et al.
2010/0017370 A1 1/2010 Carr et al.
2011/0052554 A1 3/2011 Zakrzewski et al.
2011/0158957 A1 6/2011 Bonini et al.
2011/0289035 A1 11/2011 Stojadinovic et al.
2012/0034157 A1 2/2012 Hyde et al.
2012/0060230 A1 3/2012 Collingwood et al.
2012/0302466 A1 11/2012 Sentman
2012/0321667 A1 12/2012 Sentman
2013/0115617 A1 5/2013 Wilson
2013/0149337 A1 6/2013 Cooper et al.
2013/0156794 A1 6/2013 Eshhar et al.
2013/0280220 A1* 10/2013 Ahmed .................. C12N 15/85 424/93.21
2013/0287752 A1 10/2013 Davila et al.
2013/0315884 A1 11/2013 Galetto et al.
2014/0120622 A1 5/2014 Gregory et al.
2014/0134142 A1 5/2014 Smith et al.
2014/0271579 A1 9/2014 Hyde et al.
2014/0271581 A1* 9/2014 Hyde ....................... C12Q 1/68 424/93.21

FOREIGN PATENT DOCUMENTS

WO WO 2006/020258 A2 2/2006
WO WO 2011/059836 A2 5/2011
WO WO 2012/079000 A4 6/2012
WO WO 2013/123061 A1 8/2013

OTHER PUBLICATIONS

Wikipedia: ICD-10. Accessed online on Jun. 3, 2016, 8 pages.*
Morgan et al.; "Case Report of a Serious Adverse Event Following the Administration of T Cells Transduced With a Chimeric Antigen Receptor Recognizing ERBB2"; Molecular Therapy; Apr. 2010; pp. 843-851; vol. 18, No. 4; The American Society of Gene & Cell Therapy.
Patel et al.; "T-cell killing of heterogenous tumor or viral targets with bispecific chimeric immune receptors"; Cancer Gene Therapy; 2000; pp. 1127-1134; vol. 7, No. 8; Nature America, Inc.
Araki et al.; "Comparative analysis of right element mutant *lox* sites on recombination efficiency in embryonic stem cells"; BMC Biotechnology; 2010; pp. 1-9; vol. 10, No. 29.
Araki et al.; "Targeted integration of DNA using mutant *lox* sites in embryonic stem cells"; Nucleic Acids Research; 1997; pp. 868-872; vol. 25, No. 4; Oxford University Press.
Baldi et al.; "A Bayesian framework for the analysis of microarray expression data: regularized t-test and statistical inferences of gene changes"; Bioinformatics; 2001; pp. 509-519; vol. 17, No. 6; Oxford University Press.
Bennett et al.; "Fine Tuning of T Cell Receptor Avidity to Increase HIV Epitope Variant Recognition by Cytotoxic T Lymphocytes"; AIDS; Nov. 13, 2010; pp. 2619-2628; vol. 24, No. 17.
Berger et al.; "Adoptive transfer of effector CD8+ T cells derived from central memory cells establishes persistent T cell memory in primates"; The Journal of Clinical Investigation; Jan. 2008; pp. 294-305; vol. 118, No. 1.
Casucci et al.; "Suicide Gene Therapy to Increase the Safety of Chimeric Antigen Receptor-Redirected T Lymphocytes"; Journal of Cancer; 2011; pp. 378-382; vol. 2; Ivyspring International Publisher.
Chimeric antigen receptor from Wikipedia; printed on Mar. 4, 2013; pp. 1-9; located at http://en.wikipedia.org/wiki/Chimeric_antigen_receptor.

(Continued)

*Primary Examiner* — Ilia Ouspenski

(57) ABSTRACT

Embodiments described herein relate to methods, devices, and computer systems thereof for the derivation of T CAR libraries (Universal Subject or Individual Subject) for personalized treatment of disease in a subject. In certain embodiments, differential screening of normal and diseased tissue expression data is utilized to determine disease-specific antigens and thereby generate T CAR cells reactive to such antigens to form a disease-specific library. In certain embodiments, determination of the most effective T CAR clones from the disease-specific library is based on the subject's own disease-specific antigens. In certain embodiments, a subject is treated with a therapeutically effective amount of T CAR clones.

5 Claims, 7 Drawing Sheets

(56) References Cited

OTHER PUBLICATIONS

Curtis et al.; "The genomic and transcriptomic architecture of 2,000 breast tumours reveals novel subgroups"; Nature; Jun. 21, 2012; pp. 346-352; vol. 486; Macmillan Publishers Limited.
Da Cunha et al.; "Bioinformatics construction of the human cell surfaceome"; PNAS; Sep. 29, 2009; pp. 16752-16757; vol. 106, No. 39.
De Kruif et al.; "Rapid selection of cell subpopulation-specific human monoclonal antibodies from a synthetic phage antibody library"; Immunology; Apr. 1995; pp. 3938-3942; vol. 92; Proc. Natl. Acad. Sci. USA.
Deniger et al.; "Bispecific T-cells Expressing Polyclonal Repertoire of Endogenous γδ T-cell Receptors and Introduced CD19-specific Chimeric Antigen Receptor"; Molecular Therapy; Mar. 2013; pp. 638-647; vol. 21, No. 3; The American Society of Gene & Cell Therapy.
Ermolaeva et al.; "Data management and analysis for gene expression arrays"; Nat Genet; Sep. 1998; pp. 19-23; vol. 20, No. 1; Abstract only (one page).
Getz et al.; "Coupled two-way clustering analysis of gene microarray data"; PNAS; Oct. 24, 2000; pp. 12079-12084; vol. 97, No. 22.
Illumina Gene Expression Profiling; Technical Bulletin; "Whole-Genome Expression Analysis Using the Sentrix® Human-6 and HumanRef-8 Expression BeadChips"; bearing a date of Jun. 28, 2005; 8 pages; Illumina, Inc.
Jacobson et al.; "Time to put the CAR-T before the horse"; Blood; Nov. 3, 2011; pp. 4761-4762; vol. 118, No. 18; The American Society of Hematology.
Kischel et al.; "Cell Membrane Proteomic Analysis Identifies Proteins Differentially Expressed in Osteotropic Human Breast Cancer Cells"; Neoplasia; Sep. 2008; pp. 1014-1020 + Figure W1 and Table W1 (2 pgs.); vol. 10, No. 9; Neoplasia Press, Inc.
Kloss et al.; "Combinatorial antigen recognition with balanced signaling promotes selective tumor eradication by engineered T cells"; Nature Biotechnology; Dec. 12, 2012; pp. 1-6; Nature America, Inc.
Lee et al.; "Selection of scFvs specific for HBV DNA polymerase using ribosome display"; Journal of Immunological Methods; 2004 and bearing a date of Oct. 16, 2003; pp. 147-157; vol. 284; Elsevier B.V.
Mack et al.; "A small bispecific antibody construct expressed as a functional single-chain molecule with high tumor cell cytotoxicity"; Immunology; Jul. 1995; pp. 7021-7025; vol. 92; Proc. Nat. Acad. Sci USA.
McKee et al.; "T cell avidity and tumor recognition: implications and therapeutic strategies"; Journal of Translational Medicine; published Sep. 20, 2005; pp. 1-12; vol. 3, No. 35; BioMed Central Ltd.
Mortazavi et al.; "Mapping and quantifying mammalian transcriptomes by RNA-Seq"; Nature Methods; Jul. 2008; pp. 621-628; vol. 5, No. 7; Nature Publishing Group.
Müller-Hartmann et al.; "High-throughput transfection and engineering of primary cells and cultured cell lines—an invaluable tool for research as well as drug development"; Expert Opin. Drug Discov.; 2007; pp. 1453-1465; vol. 2, No. 11; Informa UK Ltd.
Park et al.; "Treating cancer with genetically engineered T cells"; Trends in Biotechnology; Nov. 2011; pp. 550-557; vol. 29, No. 11.
Phuphanich et al.; "Phase I trial of a multi-epitope-pulsed dendritic cell vaccine for patients with newly diagnosed glioblastoma"; Cancer Immunol Immunother; published online Jul. 31, 2012; 11 pages; Springer.
Rader et al.; "Phage display of combinatorial antibody libraries"; Current Opinion in Biotechnology; 1997; pp. 503-508; vol. 8; Current Biology Ltd.
Serup et al.; "Partial Promoter Substitutions Generating Transcriptional Sentinels of Diverse Signaling Pathways in Embryonic Stem Cells and Mice"; Disease Models & Mechanisms; published online Aug. 10, 2012; 42 pages.
Viganò et al.; "Functional Avidity: A Measure to Predict the Efficacy of Effector T Cells?"; Clinical and Developmental Immunology; Oct. 22, 2012; 14 pages; Hindawi Publishing Corporation.
Xu et al.; "An Integrated Genome-Wide Approach to Discover Tumor-Specific Antigens as Potential Immunologic and Clinical Targets in Cancer"; Cancer Res.; Dec. 15, 2012; pp. OF1-OF9; vol. 72, No. 24; American Association for Cancer Research.
Yu et al.; "Circulating tumor cells: approaches to isolation and characterization"; The Journal of Cell Biology; bearing a date of 2011; pp. 373-382; vol. 192, No. 3; The Rockefeller University Press.
PCT International Search Report; International App. No. PCT/US2014/023650; Jun. 26, 2014; pp. 1-4.
Cartellieri et al.; "Chimeric Antigen Receptor-Engineered T. Cells for Immunotherapy of Cancer"; Journal of Biomedicine and Biotechnology; bearing a date of Feb. 15, 2010; 13 pages; vol. 2010; Hindawi Publishing Corporation.
Cavallin et al.; "Molecular and Cellular Mechanisms of KSHV Oncogenesis of Kaposi's Sarcoma Associated with HIV/AIDS"; Jul. 2014; pp. 1-4; vol. 10 Issue 7; PLOS Pathogens.
De Vriese et al.; "Con: Biomarkers in glomerular diseases: putting the cart before the wheel?"; Polar Views in Nephrology; 2015; pp. 885-890; Oxford University Press.
Fang et al.; "Biomarkers of Parkinson's Disease"; 2015; pp. 1009-1030; Springer Science+Business Media Dordrecht.
Jacobs et al.; "Inefficacy of Therapeutic Cancer Vaccines and Proposed Improvements. Casus of Prostate Cancer"; Anticancer Research 34; 2014; pp. 2689-2700.
Nikolova et al.; "In Search of Biomarkers for Idiopathic Scoliosis: Leptin and BMP4 Functional Polymorphisms"; Journal of Biomarkers; 2015; pp. 1-6; Hindawi Publishing Corporation.
Walsh et al.; "In search of biomarkers for autism: scientific, social and ethical challenges"; Nature Reviews—Neuroscience; Oct. 2011; pp. 603-612; vol. 12; Macmillan Publishers Limited.
Hudecek et al.; "The B-cell tumor-associated antigen ROR1 can be targeted with T cells modified to express a ROR1-specific chimeric antigen receptor"; Blood Journal; Nov. 25, 2010; pp. 4532-4541; vol. 116, No. 22; The American Society of Hematology.
European Patent Office, Supplementary European Search Report, Pursuant to Rule 164 EPC; App. No. EP 14773595; Jul. 20, 2016 (received by our Agent on Jul. 28, 2016); pp. 1-8.
Hanada et al.; "Double or nothing on cancer immunotherapy"; News and Views; Jan. 1, 2013; pp. 1-2; vol. 31, No. 1; Nature America, Inc.
European Patent Office, Supplementary European Search Report, Pursuant to Rule 62 EPC; App. No. EP 14773595; Jul. 20, 2016 (received by our Agent on Nov. 3, 2016); pp. 1-12.
Hanada et al.; "Double or nothing on cancer immunotherapy"; Nature Biotechnology; Jan. 2013; pp. 33-34; vol. 31, No. 1; Nature America, Inc.
Kloss et al.; "Combinatorial antigen recognition with balanced signaling promotes selective tumor eradication by engineered T cells"; Nature Biotechnology; Jan. 2013; pp. 71-76; vol. 31, No. 1; Nature America, Inc.
Turtle et al.; "Engineered T Cells for anti-cancer therapy"; Current Opinion in Immunology; Jul. 18, 2012; pp. 633-639; vol. 24, No. 5; Elsevier Ltd.
Uttenthal et al.; "Challenges in T Cell receptor gene therapy"; The Journal of Gene Medicine; May 4, 2012; pp. 386-399; vol. 14, No. 6; John Wiley & Sons, Ltd.
Wilkie et al.; "Dual Targeting of ErbB2 and MUC1 in Breast Cancer Using Chimeric Antigen Receptors Engineered to Provide Complementary Signaling"; Journal of Clinical Immunology; Apr. 17, 2012; pp. 1059-1070; vol. 32, No. 5; Springer Science + Business Media, LLC.
Kenworthy et al.; "Dynamics of putative raft-associated proteins at the cell surface"; The Journal of Cell Biology; Jun. 7, 2004; pp. 735-746; vol. 165, No. 5; www.jcb.org.
Jungbluth et al.; "Immunohistochemical Analysis of NY-ESO-1 Antigen Expression in Normal and Malignant Human Tissues"; Int. J. Cancer; Jan. 19, 2001; pp. 856-860; vol. 92; Wiley-Liss, Inc.

* cited by examiner

Multi-Specific TCAR recognizes
2 different epitopes of one antigen.

Multi-Specific CAR recognizes
2 different antigens.

COMPOSITIONS, METHODS, AND COMPUTER SYSTEMS RELATED TO MAKING AND ADMINISTERING MODIFIED T CELLS

If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application is related to and/or claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)). In addition, the present application is related to the "Related Applications," if any, listed below.

PRIORITY APPLICATIONS

None.

RELATED APPLICATIONS

U.S. patent application Ser. No. 13/826,803, entitled COMPOSITIONS, METHODS, AND COMPUTER SYSTEMS RELATED TO MAKING AND ADMINISTERING MODIFIED T CELLS, naming Roderick A. Hyde, Wayne R. Kindsvogel and Gary L. McKnight as inventors, filed 14 Mar. 2013 with, is related to the present application.

U.S. patent application Ser. No. 13/827,960, entitled COMPOSITIONS, METHODS, AND COMPUTER SYSTEMS RELATED TO MAKING AND ADMINISTERING MODIFIED T CELLS, naming Roderick A. Hyde, Wayne R. Kindsvogel and Gary L. McKnight as inventors, filed 14 Mar. 2013 with, is related to the present application.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, *Benefit of Prior-Filed Application*, USPTO Official Gazette Mar. 18, 2003. The USPTO further has provided forms for the Application Data Sheet which allow automatic loading of bibliographic data but which require identification of each application as a continuation, continuation-in-part, or divisional of a parent application. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above and in any ADS filed in this application, but expressly points out that such designation(s) are not to be construed in any way as any type of commentary and/or admission as to whether or not the present application contains any new matter in addition to the matter of its parent application(s).

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

SUMMARY

Various embodiments described herein relate to compositions, methods, and computer systems for constructing T cell clone(s) exhibiting an artificial Chimeric Antigen Receptor(s) as part of a library. Various embodiments described herein relate to administering the T cell clone cell line(s) from the library to a subject in need thereof.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1A:
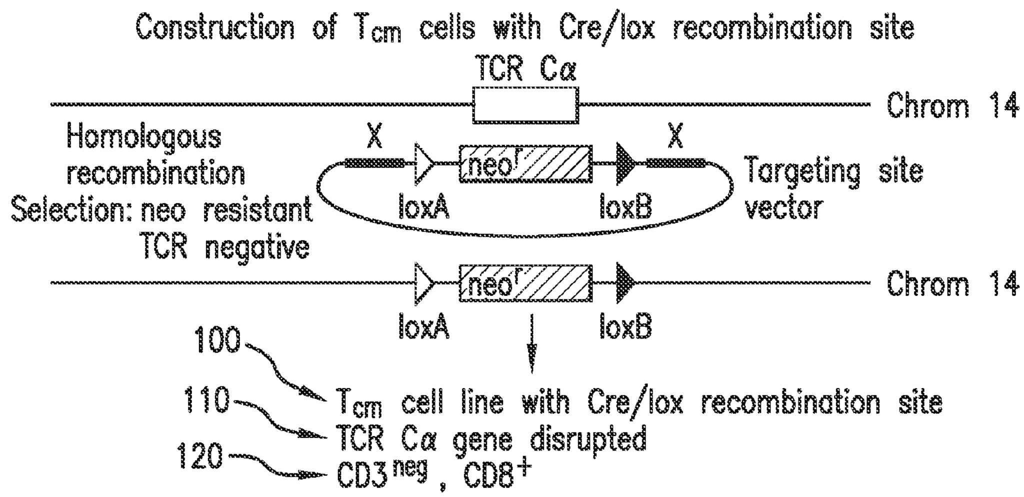
FIG. 1A is a partial view of an embodiment related to engineering an artificial T cell line.

In the following detailed description, reference is made to the accompanying drawings, which form a part hereof In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Described herein are various embodiments related to Universal Subject Disease Specific Library of cytolytic T CAR cells (T cells with artificial Chimeric Antigen Receptors) and Individual Subject Disease Specific Library of cytolytic T CAR cells. In an embodiment, the T CAR cells represent a universal T cell clone that has been manipulated to artificially and specifically recognize a particular target antigen (e.g., a disease specific antigen). In an embodiment, the T CAR cells provide a tool for immunotherapy of a subject afflicted with a disease or disorder. Also described herein are computer systems utilized in conjunction with the methods of making or administering the T CAR cell libraries to a subject.

Artificial Cytolytic T Cell Clone Universal Subject Disease Specific Library

In an embodiment, a Universal Subject Disease Specific Library of artificial cytolytic T cells is developed that bear a multi-specific artificial chimeric antigen receptor (CAR), as described in detail herein. In an embodiment, the development of a multi-specific T cell CAR clone Universal Subject Disease Specific Library provides an HLA-independent recognition of antigen. In an embodiment, the library provides a rapid and effective treatment of immune-related disorders and diseases. In an embodiment, the library is utilized to make a disease specific therapeutic T cell line. Such CAR is engineered, for example, by using available sequence data or expression data derived from population studies of multiple tissue types from multiple subjects. From this data, in an embodiment antigens are identified from all presently identified cell surface antigens and secreted proteins for a particular species of subject (e.g., human), or from all identified cell surface antigens and secreted proteins for a specific tissue type (e.g. breast cancer tissue), based on tumor or diseased tissue vs. normal tissue. This differential expression screen identifies antigens specifically associated with various tissues, of either normal or diseased state.

In an embodiment, the expression data are determined by screening primary tumor tissue against normal tissue. In an embodiment, the expression data are determined by screening primary tumor tissue against secondary tumor tissue. In an embodiment, the expression data are determined by screening primary tumor tissue or secondary tumor tissue against metastasized tissue.

In an embodiment, a subject includes a mammal, bird, fish, reptile, or amphibian. In an embodiment, a subject includes a vertebrate or invertebrate. In an embodiment, a subject includes a plant. In an embodiment, a subject includes a human. In an embodiment, the subject includes a fetus in utero.

In an embodiment, the genetic expression data are derived from multiple tumors from many subjects in order to provide an array of disease specific antigens. Thus, in an embodiment, multiple disease sites from multiple diseased subjects are utilized for sampling of genetic expression data, or multiple cell samples from a diseased subject. For example, in an embodiment, the expression data are derived from multiple disease sites (e.g., joint synovial fluid and/or cell samples) from multiple subjects afflicted with rheumatoid arthritis or systemic lupus erthematosus. In an embodiment, the expression data are derived from multiple central nervous system (e.g., spinal tap) fluid and/or cell samples, from multiple subjects afflicted with multiple sclerosis. In an embodiment, the expression data are derived from multiple colon biopsies, from multiple subjects afflicted with Crohn's disease or Inflammatory Bowel Disease. In an embodiment, the expression data are derived from multiple sputum or saliva samples, from multiple subjects afflicted with asthma. In an embodiment, the expression data are derived from multiple blood samples, from multiple subjects afflicted with diabetes, Graves' disease, Hashimoto's thyroiditis, Myasthenia gravis, vasculitis, or other immune related disorder. These are non-limiting examples of tissues that may be tested for comparison with normal tissue from either the same subject or from a healthy subject not afflicted with the same disease or disorder as the testing subject. It is understood that various tissues (including lymph, blood, saliva, urine, or other bodily fluid and/or cell sample) may be utilized for testing for cell surface expression of antigens and secreted proteins related to a particular disease or disorder.

In an embodiment, a library of T cell CAR clones is constructed for each particular tissue type or state of diseased tissue type. For example, a library can be constructed for primary tumors in breast cancer, a separate library can be constructed for secondary tumors in breast cancer, and a separate library can be constructed for metastatic breast cancer. In another example, a library can be constructed for multiple sclerosis, a separate library for Alzheimer's disease. In another example, a library can be constructed for early stage Alzheimer's disease, and a separate library constructed for later state Alzheimer's disease. It is understood that these are non-limiting examples and can readily be applied to other tissue types or diseases.

In an embodiment, the tissue type for purposes described herein includes but is not limited to, breast tissue, prostate tissue, colon tissue, stomach tissue or other gastro-intestinal tissue, uterine tissue, eye tissue, ear tissue, skin tissue, blood, nasal tissue, mouth or throat tissue (such as oral mucosa, pharyngeal or laryngeal tissue, tongue) joint tissue, bone tissue, bone marrow tissue, scalp tissue, muscle tissue, ovarian tissue, testicular tissue, or fetal tissue.

In an embodiment, a computer algorithm is used to prioritize the most commonly expressed cell surface antigens for targeting in the engineering of the artificial T CAR cell clones or the spatial or temporal expression of one or more antigens. The T CAR cell clones are utilized for adoptive T cell therapy as a treatment modality for immunotherapy for tumor regression in cancer, or other immunological illnesses or afflictions. However, if a T CAR library is generated with each CAR recognizing only one antigen (with or without recognizing multiple epitopes of the only one antigen), then the library is "universal," and can be utilized for any human disease. In this case, a computer algorithm is used to prioritize the most commonly expressed cell surface antigens for a particular disease or cell/tissue type.

For example, a computing device or computing system running an algorithm or computer program is used to select the top several most-commonly expressed cell surface antigens and secreted proteins specified for a particular target tissue. The cell surface antigens and secreted proteins can be determined by FACS, gene microarray, RT-PCR, etc. or other standard techniques. In another example, a computer algorithm can be used to select antigens based on their structural formation, post-translational modification, Kd value based on previously identified antibodies, genetic sequence, mRNA sequence, peptide sequence, or other characteristic(s).

Many computer software analysis algorithms and programs have been developed to analyze expression data. For example, the expression data can be analyzed with Significance analysis of microarrays (SAM) developed by Stanford, ANOVA, ANOSVA (for analysis of splice variation), Bonferroni, Bayesian probability, Markov chains, Monte Carlo methods, or Gaussian distributions. See, for example, Baldi, et al. Bioinformatics, vol. 17, no. 6, 2001, pp. 509-519, which is incorporated herein by reference.

Based on the analysis of the information of the population diseased tissue expression studies, a multi-specific T CAR cell clone library is constructed as described below. For example, targeting of specific tumor specific antigen (TSA) groups or subgroups can be correlated by analyzing expression studies of genomic and transcription changes. For example, inherited variants (copy number variants and single nucleotide polymorphisms) and acquired somatic copy number aberrations (CNAs) have been shown to be associated with expression in roughly 40% of genes, with the dominant being cis- and trans-acting CNAs. See Curtis, et al. Nature, vol. 486, pp. 346-352, 2012, which is incorporated herein by reference.

In an embodiment, a published genomic listing is utilized that identifies all presently identified cell surface antigens on human cells. See, for example, Cunha, et al. PNAS, 106: 16752-16757 (2009), which is incorporated herein by reference. In an embodiment, utilizing this genetic sequence listing of cell surface antigens, T CAR cells are constructed with single chain antibodies providing specific binding to one or more cell surface antigens on human cells. For example, single chain variable region fragments (scFvs) which specifically bind to a single cell surface antigen from the listing are identified, for example, by screening phage display libraries comprised of human scFv. More details are included in Example 3 herein. Thus, in an embodiment, multi-specific T CAR cells are engineered for each of the presently identified human cell surface antigens (approximately 3700 proteins), and optionally various combinations thereof. For example, in an embodiment, a T CAR recognizes only one antigen. In an embodiment, a T CAR recognizes multiple antigens.

Likewise, in an embodiment, a series of Western blots is conducted between normal tissue and diseased tissue from multiple subjects, or arrays, RT-PCR (optionally quantitative real-time, etc.), and other techniques are utilized for detecting glycosylation or post-translational modifications. In this way, in an embodiment, the target antigens are identified based on differences in genetic sequence, mRNA sequence, or post-translational modification (e.g., glycosylation), and from the identified target antigens, T CAR cells are constructed. In an embodiment, mRNA isolated from a disease site in a subject is sequenced and the sequence information compared by computer system with the identified sequences. In an embodiment, such a differential screening out of the normal sequences and identification of abnormal gene expression sequences is utilized to identify the target antigens for the disease of the subject.

It is understood that an antigen, as recognized by one of skill in the art, includes a substance capable of the lock-and-key interaction of one molecule (the antigen) with another (the antibody or lymphocyte receptor). It is further understood that an antigen includes peptides, glycopeptides, peptidoglycans, lipids, proteoglycans, glycoproteins, glycolipids, and the like. It is understood that antigen specificity includes the ability of a lymphocyte (e.g., T CAR cell) to recognize an antigen specifically as a unique molecule and discern it from another antigen with a high level of precision. Antigen specificity is attributed to the primary, secondary, and tertiary structure, including side-chain conformations of the antigen. Moreover, an epitope includes the portion of the antigen that provides the recognition of the antigen by the lymphocyte receptor (e.g., T CAR cell).

Next, based on the selected antigens derived from the expression data described above, an array of single chain variable fragments (scFv) are identified through the use of identified antibodies against the particular antigens, or by way of screening the scFvs for the antigen(s) if antibodies are not yet readily available. In an embodiment, the selection of scFvs is conducted for example, by way of phage display, as described herein. In an embodiment, the selection of scFvs is conducted by way of ribosome display. See, for example, Lee et al. JIM, 284 (2004) 147-157, which is incorporated herein by reference. In an embodiment the selection of scFvs is conducted by way of expression in transgenic organism (e.g., plant or animal).

Therefore, in an embodiment, regardless of how the sequences of target antigens are derived, once such sequences have been obtained, a pair of scFvs will be developed for each pair of antigens and the scFvs will be incorporated into a CAR, an artificial T cell Chimeric Antigen Receptor. The corresponding sequences are converted into a retroviral (e.g., lentiviral) vector, for example, according to standardized techniques. In an embodiment, the expression vector(s) and utilized to infect T cells, thus resulting in a universal T cell clone that has been manipulated to artificially and specifically recognize a particular target antigen. The summation of all such target-specific T CAR cell clones comprises the T CAR cell library of clones.

In an embodiment, each T cell clone bears a multi-specific CAR that elicits a polyclonal response by targeting multiple epitopes of the same antigen, which is usually much stronger than a monoclonal reaction between a T cell and an antigen. In addition, the polyclonal response of the T CAR cell may be more efficacious in a clinical setting. (See, for example, Phuphanich, et al. Cancer Immunol. 62: 125-135, 2013, which is incorporated herein by reference).

In an embodiment, the T cell CAR is engineered to include two or more, three or more, four or more, five or more, six or more, seven or more, eight or more, nine or more, or ten or more target sequence specific binding sites. This multi-specific CAR provides a higher level of specificity, and thus increased binding strength, for the target tissue. In an embodiment, the data expression analysis determines a distinctive antigen profile for a specific tissue disease or disease state. For example, utilizing heterogeneous expression profile analysis, it was found that among tumor-specific antigens, serum autoantibodies against seven candidate targets were detected in 4-11% of patients with lung and stomach cancers. See, for example, Xu et al. Cancer Res. 72(24):1-11 (2012), which is incorporated herein by reference. A similar algorithm applied in Xu is adapted for use in certain embodiments described herein. In an embodiment, coupled two-way clustering analysis of the expression data is employed. See, for example, Getz et al. PNAS 97; 22 (2000) 12079-12084, which is incorporated herein by reference. In an embodiment, a web-browser interface based database such as ArrayDB, is utilized for expression data analysis. See for example, Ermolaeva, et al. Nat. Genet. 1998 (20)1: 19-23 (1998), which is incorporated herein by reference.

Thus, in an embodiment, for the Universal Subject Disease Specific Library, a differential screen is performed by comparing cell expression data of diseased cells (e.g., tumor cells) from multiple cell samples (e.g., multiple tissues or organs) of multiple subjects, with normal tissue from multiple cell samples of multiple subjects. The parameters for normal tissue expression can be adjusted for example, in order to reduce background noise or fine-tuned in order to deduce a true differential expression for a particular target antigen.

The resulting data from this differential screen is manipulated by a computer (based on quantity of expression of antigen(s), quality of expression of antigen(s), Kd of binding of antigen(s) to cognate receptor(s) or antibody, or other characteristics) and derives the Universal Subject Disease Specific Antigens (UDSA) for a particular disease or disorder. In an embodiment, The UDSA are measured or categorized quantitatively and/or qualitatively. That is, in an embodiment, the UDSA and gene expression information related thereto are cataloged or organized based on the relative quantity of expression in the diseased tissue (e.g., the quantity of antigens, n=about 1, about 2, about 3, about 4, about 5, about 6, about 7, about 8, about 9, about 10, about 11, about 12, about 13, about 14, about 15, about 16, about 17, about 18, about 19, about 20, about 30, about 40, about 50, or any value therebetween), and/or based on the quality of the expression in the diseased tissue (e.g., genetic or mRNA sequence, glycosylation or other post-translation modifications, etc.). In an embodiment, the UDSA and gene expression information related thereto are cataloged or organized based on one or more of a genetic or mRNA mutation, abnormal post-translational modification, Kd value that varies for antigen-receptor binding, methylation/acetylation of nucleic acids, lipid modifications, or other structural characteristics. Thus, the gene expression information includes any of the qualitative or quantitative characteristics disclosed herein.

For example, glycosylation or other post-translational modifications are analyzed by way of sequencing, linkage analysis (e.g., enzymatic cleavage or otherwise), carbohydrate separation methods (e.g., high-performance liquid chromatography), and other means. Likewise, genetic or mRNA sequence aberrations or mutations can be detected by sequencing, enzymatic cleavage, or other standard techniques.

In an embodiment, the UDSA and gene expression information related thereto are cataloged or organized based on one or more of the total number of antigens expressed in a diseased tissue versus normal tissue, the relative number of antigens expressed in a diseased tissue versus normal tissue, a cluster expression of several particular antigens in a diseased tissue versus normal tissue, the absence of expression of a normal tissue antigen in a diseased tissue, cell surface density of a single antigen, cell surface concentration of a single antigen, or number of copies of an antigen per cell.

The UDSA are then utilized to make a Universal Subject Disease Specific Library of multi-specific CARs that recognize disease specific antigens found most commonly in the general population of subjects. Details of the molecular biology of making the Universal Subject Disease Specific Library are discussed further herein. Once the Universal Subject Disease Specific Library has been generated, a subject afflicted with the particular disease for which the UDSAs have been identified has its own diseased cell samples analyzed for cell expression. Based on the results of the subject's own diseased cell sample analysis, a computer system is utilized to select multi-specific clones from the Universal Subject Disease Specific Library that match the subject's own diseased cell expression profile. In this way, the subject receives multi-specific clones designed specifically for its individual treatment based on its own diseased cell sample expression data. In an embodiment, multiple libraries are generated each based on various stages of disease (e.g., progressive chronic diseases, metastatic cancer, etc.) compared with normal tissue or other disease states of the tissue.

By contrast, in an embodiment, for the Individual Subject Disease Specific Library, a differential screen is performed by comparing cell expression data of the subject's own diseased cells (e.g., tumor cells), with normal tissue from the same subject. In an embodiment, if multiple tissues or organs are afflicted (e.g., metastasis of a tumor), then each tissue or organ is included in separate expression analysis or the same expression analysis, depending on the desired treatment regimen. For example, in a subject with no histologically detected metastasis of the primary tumor or disease site, the expression analysis is conducted with the primary tumor vs. normal tissue antigen profile. In an embodiment, the expression analysis includes the individual's specific disease analysis of primary tumor vs. normal tissue and further includes analysis to select antigens from a universal metastasis antigen profile, even if no metastases is present or detected in this particular subject. In that way, a prophylactic treatment to target metastases is conducted in conjunction with the specific primary disease antigen profile. In another example, the expression analysis includes the individual's primary disease site antigen profile as well as secondary disease sites (e.g., metastases). In this way, multiple targets of disease are attacked efficiently and effectively.

In an embodiment, a multi-specific CAR specifically recognizes two or more epitopes of the same antigen. In an embodiment, the physical proximity of the multi-specific CAR that specifically recognizes two or more epitopes of the same antigen provides a benefit in that the likelihood of receptor binding is increased and clustering of multiple separate antigen receptors at the T cell surface is not needed since the multi-specific receptors are physically located on the same CAR.

In an embodiment, a computing device or computing system running an algorithm or computer program is used to analyze the Kd binding strengths of the multi-specific CAR, for example, by analysis of the binding strength of each selected antigen binding site with its target sequence, as well as the coordinated binding strength of the entire multi-specific receptor. For example, in certain CARs the spatial pattern of the multiple specific target sites is optimized based on the sequence in which the specific antigen sites occur in the CAR, or based on the spatial binding relationship with the particular targets. In an embodiment, the multi-specific CAR provides at least 2 or more, at least 3 or more, at least 4 or more, at least 5 or more, at least 6 or more antigen binding sites (indicating receptor specificity) (e.g., scFvs). In an embodiment, one or more multi-specific CARs are included on a single T cell clone. In an embodiment, two or more, three or more, or four or more multi-specific CARs are included on a single T cell clone.

In an embodiment, the T cell clone is constructed by assembling the specific nucleotide sequences selected by, for example, splice overlap PCR and standard cloning methods. See, for example, U.S. Pat. No. 6,410,319, which is incorporated herein by reference. Utilizing standard cloning techniques (e.g., RT-PCR), ribosome binding sequences, signal peptides (e.g., OX40 or 41BB), and the particular sequences selected for determining the specificity of targeting for that individual clone as well as any desired linkers, are spliced and joined together into a final genetic construct that is then cloned into a mammalian expression vector (e.g., pcDNAneo or similar vector, under the control of a CMV immediate-early or similar promoter). Proper assembly of the artificial construct is confirmed, for example, by DNA sequence analysis of the final product.

In an embodiment, T cells are then transfected with the artificial CAR construct according to standard techniques, and are analyzed (e.g., by FACS and/or Western Blot and/or Fluorescence in situ hybridization (FISH)) for confirmation that the cells harbor the non-naturally occurring construct.

In an embodiment, T cells expressing the multi-specific CAR are tested for in vitro stimulation of cytokine production, for cytolytic activity, and (where appropriate) induction of any apoptotic or "suicide" genes optionally included in the artificial CAR construct. For example, in an embodiment, the T cell clone includes a conditionally inducible suicide gene, such as thymidylate kinase, inducible caspase 9, CD20, thymidine kinase, or modified FAS. Such in vitro testing is done according to standard techniques, for example, ELISA assays for IL-2 can be utilized to test for in vitro stimulation of cytokine production (IL-2 is commonly tested since it induces cell proliferation among lymphocytes). Chromium Release Assays can be used for measuring the cytolytic activity of the clones by allowing a target cell to take up radioactive supernatant, followed by washing residual radioactivity away and incubating with the T cell clone presumed to be cytolytic. Measurement of release of the radioactivity indicates killing of the cells by the T cell clone. In vitro cell proliferation assays utilized to measure the clones' ability to proliferate themselves can also be measured by standard techniques, including, for example, my measuring tritiated thymidine (thymidine is incorporated into the DNA of dividing cells). See U.S. Pat. No. 6,410,319, incorporated herein by reference, for more details on some of these standardized techniques.

A subject afflicted by or having symptoms of a disease or disorder, for example an immune-related disease or disorder (such as cancer) is treated with the appropriate multi-specific T cell clone(s) selected from the Universal Subject Disease Specific Library based on analysis of a cell sample (e.g., biopsy) the subject's specifically selected target antigens (such as tumor specific antigens) identified by use of a microarray, FACS, or other standard technique. In this manner, the multi-specific T cell clone Universal Subject Disease Specific Library is analyzed (optionally by computing device or computing system running an algorithm to identify the optimal T cell clone based on information determined from expression studies of the subject's tissue (e.g., tumor tissue)) and the optimal T cell clones are selected for the subject. In an embodiment, the subject is treated by infusing one or more therapeutically effective dose of the cytolytic T cell clones, each expressing the particular multi-specific artificial CAR.

In an embodiment, prior to, during, or subsequent to infusing the subject with the first cohort of T cell CAR clones, a sample of cells (e.g., from a biopsy) from the subject's tumor or other target tissue is extracted and tested for cytolysis with the selected T cell CAR clones expected to be used for therapy. In this way, the relative cytolysis is determined, allowing for a more accurate dosing range and schedule for the subject's therapy without causing undue cytotoxicity. Such dosing and scheduling are performed as for any standard clinical trials or testing, and may include one or more parameters specific to the individual test subject.

Artificial Cytolytic T Cell Clone Individual Subject Disease Specific Library

In an embodiment, an Individual Subject Disease Specific Library of cytolytic T cells expressing an artificial chimeric antigen receptor (CAR), as described in detail herein, is personalized specifically to an individual subject's own disease (e.g., tumor) antigen expression data or expression patterns, rather than population expression studies. For example, by screening the Universal Subject Disease Specific Library for a particular tissue or disease with an individual subject's diseased tissue, antigens specific for the individual subject's diseased tissue are identified and isolated. In an embodiment, this information provides the basis for determining and/or constructing appropriate T CAR cell clones for therapeutic administration to the individual subject. In an embodiment, a database of previously identified antigen sequences is screened with the Individual Subject's diseased tissue and/or sequences therefrom in order to determine the specific disease antigens associated with the Individual Subject's disease.

In an embodiment, the disease specific library is utilized to generate a disease specific therapeutic T cell line. Such CAR is engineered, for example, as described herein for the Universal Subject Disease Specific Library, except that in order to generate the CAR for the Individual Subject Disease Specific Library, sample cells (e.g., from a biopsy) from the subject afflicted with cancer or another immune disease are subjected to, for example, Next Generation Sequencing (NGS) which is a standard technique that provides a fast, high-quality sequence of the mRNA transcriptome of the sample cells. See, for example, Mortazavi, et al., Nature Methods 5:621-628, 2008, which is incorporated herein by reference). For example, a differential screening of tumor vs. normal cell mRNA can be conducted for an individual subject with specific disease. The standard techniques of constructing the T CAR cell clones and library described herein for the Universal Subject library can be utilized for the Individual Subject Library.

As similarly described for the Universal Subject Disease Specific Library, in an embodiment, a computer algorithm is used to prioritize the most commonly expressed cell surface antigens and secreted proteins for targeting in the engineering of the artificial cytolytic T CAR cells, or the spatial or temporal expression of one or more antigens (e.g., Protease-activated receptors (PAR receptors) are a G protein-coupled receptors that are activated by cleavage of part of their extracellular domain). The T cell CAR clones are utilized for adoptive T cell therapy as a treatment modality for immunotherapy for tumor regression in cancer, or other immunological illnesses or afflictions. The remainder of the process of constructing and utilizing the cytolytic T cell CAR clones is carried out in the same manner as described for the Universal Subject Disease Specific Library herein.

Based on the analysis of the mRNA transcriptome information of the subject's tumor, a multi-specific T cell CAR clone library is constructed in a similar manner as described for the Universal Subject Disease Specific Library herein.

The resulting data from this differential screen is manipulated by a computer (based on quantity of expression of antigen(s), quality of expression of antigen(s), Kd of binding of antigen(s) to cognate receptor(s) or antibody, or other characteristics) and derives the Individual Disease Specific Antigens (IDSA) for the individual subject's particular disease or disorder. In an embodiment, where an Individual Subject is afflicted with multiple diseases simultaneously or sequentially, one or more Individual Subject Disease Specific Libraries are generated—each for use with one particular disease or disorder. Thus, if a subject is afflicted with multiple sclerosis, and later contracts kidney cancer, that subject can be treated with clones from a library specific for the subject's multiple sclerosis, and later for the subject's kidney cancer. In an embodiment, the IDSA are measured or categorized quantitatively and/or qualitatively, similarly as described herein for the Universal Subject Disease Specific Library.

The IDSA are then utilized to make an Individual Subject Disease Specific Library of multi-specific CARs to disease specific antigens found most commonly in the subject's own diseased cells. Details of the molecular biology of making the Individual Subject Disease Specific Library are discussed further herein. Once the Individual Subject Disease Specific Library has been generated, a computer system is utilized to select multi-specific clones from the Library for use in various treatment sequences or dosages. In this way, the subject receives customized treatment for its own cell expression based on its diseased cells.

Construction of Multi-Specific CAR for Either Universal Library or Individual Subject Library In an embodiment, the multi-specific CAR is genetically engineered as an artificial T cell receptor specifically targeting the computer-selected IDSA or UDSA. For example, in an embodiment, the CAR is a cell surface molecule including one or more extracellular domain (the specific targeting region of the receptor), one or more intracellular signaling domain, and one or more transmembrane domain.

In an embodiment, the CAR genetically disrupts the innate T cell receptor of the engineered cell. In an embodiment, the genetic disruption of the innate T cell receptor results in the complete elimination of the innate T cell receptor function. This elimination of innate T cell receptor function operates to prevent allogeneic response (e.g., graft vs. host disease) by the T CAR cells on the subject receiving them during therapy.

In an embodiment, individual components of the T CARs are produced from nucleic acid molecules using standard molecular biology methods. For example, as described herein, nucleic acid molecules are inserted into a vector that is able to express the fusion polypeptide when introduced into an appropriate host cell (e.g., bacteria, yeast, insect, mammalian cells, or other cells). In an embodiment, any of the many standard technical methods can be used for insertion of DNA fragments into a vector, as well as for constructing an expression vector encoding the fusion polypeptides described herein and under the control of transcriptional or translational control signals. For example, one or more of these methods may be used for in vitro recombinant DNA or synthetic techniques or in vivo recombination.

In an embodiment, expression of the fusion polypeptides may be regulated by a second nucleic acid sequence wherein the polypeptide(s) is expressed in a host transformed with the recombinant DNA molecule (i.e., expression of the polypeptide may be controlled by any promoter/enhancer element utilized for standard practice.)

In an embodiment, the individual T cell clones are deficient in at least one Human Leukocyte Antigen (HLA), including for example, HLA I−, HLA II−, HLA E or HLA G+. For example, the HLA I− HLA II− is engineered by deleting the innate T cell receptor alpha region in beta2M (HLA class I−), and in HLA DR, HLA DQ or HLA DP regions (for HLA class II−). Standard methods of gene inactivation that can be utilized for this particular component include enforced methylation, siRNA, or shRNA. The HLA I− and HLA II− conditions operates to prevent host T cell elimination of the engineered T cell clone, whereas the forced expression of HLA E or HLA G operates to prevent NK cell elimination of the engineered T cells once administered to a subject.

In an embodiment, individual T cells used for generating T CAR cells can be CD4+/CD8−, CD4−/CD8+, CD4−/CD8−, or CD4+/CD8+. In an embodiment, the T cells can be a mixed population of CD4+ and CD8+ cells, or can be a population propagated from a single clone. In an embodiment, the T cells are a mixed population of CD4+ cells that produce IL-2 or other cytokines when their receptor engages the specific IDSA or UDSA, and CD8+ cells that lyse the target cells when their receptor engages the specific IDSA or UDSA. In an embodiment, T cells that have been modified as described herein are referred to as T CAR cells. In an embodiment, the T cell includes a memory T cell with a phenotype of CD62L+CD45RA−.

In an embodiment, the individual T cells are primary T CAR cells, such as from peripheral blood mononuclear cells (PBMC). In an embodiment, the individual T CAR cells are engineered from stem cells from the bone marrow, peripheral blood, hepatic, spleen, or other stem cell compartment. In an embodiment, the T CAR cells are engineered from hematopoietic stem cells. In an embodiment, the T cell CAR clones are expanded prior to or subsequent to differentiation into T cells.

In an embodiment, the target antigen(s) described herein include one or more isolated nucleic acid molecule(s). In an embodiment, the one or more isolated nucleic acid molecules include at least one of single stranded or double stranded DNA or RNA (including mRNA), or a RNA-DNA hybrid. In an embodiment, the sequence corresponds to either a full-length or partial gene sequence. In an embodiment, the sequence includes a small inhibitory RNA.

In an embodiment, the T CAR cells are utilized in a method of treating a subject afflicted with a disease or disorder related to the IDSA or UDSA. Such method of treatment is described in detail, and includes administering specific T CAR cells to the subject in a therapeutically effective amount. In an embodiment, the T CAR cells administered with one or more cytokines, including but not limited to IL-2, IL-4, IL-8, IL-6, TGF-beta, IL-10, BAFF, APRIL-, IL-23, IL-17, an Interferon member, or similar cytokine For example, it has been reported that modified T cells used in adoptive therapy are less effective if not stimulated with IL-2 to proliferate. See U.S. Pat. No. 6,410,319, which is incorporated herein by reference. However, sepsis can be induced if levels of cytokines are too high. See Jacobson and Ritz, Blood, vol. 118, no. 18, 2011, which is incorporated herein by reference. Thus, in an embodiment, the method further includes a computer-selected panel of cytokines for administration before, during, or after administration of the T CAR cells to a particular subject. The computer-selected panel of cytokines includes one or more cytokines, including the non-limiting examples set forth herein.

In an embodiment, a subject is treated through administration of a therapeutically effective dose of T CAR cells. In an embodiment, the therapeutically effective dose includes approximately $10^6$, approximately $10^7$, approximately $10^8$, approximately $10^9$, approximately $10^{10}$, approximately $10^{11}$, approximately $10^{12}$, or any value there between, T CAR cells per square meter of body surface (cells/$m^2$). In an embodiment, one or more cytokines are infused before, during, or subsequent to administration of the T CAR cells. In an embodiment, the one or more cytokines are administered in an amount of about $10^3$, about $10^4$, about $10^5$, about $10^6$, or any value therebetween, units per kilogram body weight. The dosing schedule is determined based on standard adoptive T cell therapy schedules, modified as needed for efficacy, cytotoxicity, and other parameters for clinical trials.

In an embodiment, the CAR is contained in a plasmid expression vector in proper orientation for expression, and is transfected (by electroporation, calcium phosphate, or other means) directly into the T cell. In an embodiment, the CAR is contained in a viral vector and the T cells are infected with the artificial construct.

In an embodiment, construction of the CAR is conducted, for example, by standard PCR techniques such as splice overlap. Assembly of each of one or more of: target receptor sequence, ribosome binding sequence, signal peptide, variable regions (VL, VH, etc.), a linker region, hinge region, transmembrane domain, and/or zeta chain is conducted with PCR techniques and primers either commercially available or derived from the sequence of the target IDSA or UDSA, when necessary. In an embodiment, the final constructs are flanked by restriction sites for directional subcloning into expression vectors.

As described herein, in an embodiment, the CAR is chromosomally integrated at the innate T cell receptor alpha locus. In an embodiment, the CAR is chromosomally integrated in other active chromatin regions (for example the CAR can be linked to the innate T cell receptor-like promoter region, such as the active T cell receptor V alpha or V beta region). In an embodiment, the T CAR is integrated at the rearranged site of the T cell receptor V beta or V alpha promoter in the engineered cell line. In an embodiment, each T CAR cell line is propagated with the corresponding artificial antigen presenting cell to generate the memory T CAR cell phenotype of CD62L+CD45RA−. In an embodiment, the memory T CAR cells are enriched by cell sorting (e.g., by magnetic or antibody column sorting, FACS, or other technique).

In an embodiment, in vitro propagation cell lines are utilized, such as but not limited to, Jurkat, Daudi, P815, K562, 2c, and others. In an embodiment, cells are propagated by standard cell culture techniques.

In an embodiment, the T CAR cells further include one or more magnetic particles. In an embodiment, the T CAR cells include one or more magnetic nanoparticles. In an embodiment, one or more magnetic particles are administered to a tumor or other disease site of a subject prior to, during, or subsequent to administration of one or more T CAR cells including one or more magnetic particles. In this way, the T CAR cells will be further directed to the disease site by way of the magnetic attraction by way of the magnetic particles both in the T CAR cells as well as at the disease site.

In an embodiment, the T CAR cells further include one or more radio frequency identification devices (RFIDs).

In an embodiment, as described above, prior to, during, or subsequent to infusing the subject with the first cohort of cytolytic T cell CAR clones, a sample of cells (e.g., from a biopsy) from the subject's tumor or other target tissue is extracted and tested for cytolysis with the selected T cell clones expected to be used for therapy. In this way, the relative cytolysis is determined, allowing for a more accurate dosing range and schedule for the subject's therapy without causing undue cytotoxicity.

Various embodiments described herein utilize certain conventional techniques and descriptions of molecular biology, polymer chemistry, cell biology, biochemistry, immunology, and organic chemistry.

Computer Systems

In an embodiment, one or more computer systems (including one or more computing devices) include computer-readable non-transitory media which provides methods to one or more users. In an embodiment, the user includes a human, or another computer. In an embodiment, a system includes a processor. In an embodiment, a system includes non-transitory medium memory coupled with a processor, the non-transitory medium memory storing a plurality of machine instructions that cause the processor to perform the steps described herein.

In an embodiment, computer software products are employed, that include computer readable non-transitory media including computer-executable instructions for performing certain logic steps of various methods described herein. In an embodiment, suitable computer readable non-transitory media include but are not limited to floppy disc, CD-ROM/DVD/DVD-ROM, hard-disk drive, flash memory, ROM/RAM, magnetic tapes, etc. In an embodiment, the computer executable instructions are written in a suitable computer language or combination of several languages. In an embodiment, the various computer software products are utilized for various aspects including but not limited to, data analysis, management of data, operation of one or more instruments, storage of data, and further comparison over time of stored data with new or other stored data.

In an embodiment, a computer-readable non-transitory medium includes encoded programming code for analyzing gene expression. In an embodiment, the software includes code for performing the steps of the determination described herein, and a computer-readable non-transitory medium for storing the code.

In an embodiment, the programming code applies one or more Clustering Analysis algorithms, including one or more of K-Means, principal component analysis (PCA), self-organizing maps (SOM), or iterative independent component analysis (ICA) to data including one or more measured signals to identify an optimum number of independent clusters into which the data may be grouped. In an embodiment, the programming code includes code for one or more of: removing background "noise" from the data, using Cluster Analysis to cluster data from one or more gene expression signals into an optimal number (n) of independent groups, or determine if there is a positive correlation of expression of one gene in a first group is statistically correlated with the expression of a second gene in a second group (e.g., if positive gene expression of gene X in primary diseased tissue is correlated with the expression of Y gene in metastasized diseased tissue). In an embodiment, the programming code includes code that compiles data into a form suitable for computer analysis.

In an embodiment, the differential screening includes removing "noise" or providing for normalization of the data. Thus, while receptors that bind specifically to a particular target antigen, hybridization conditions utilized can be adjusted to decrease the possibility of non-specific binding (or background noise). Likewise, in the analysis steps, the computer algorithm(s) utilized herein can provide the computational analysis such that the background noise is reduced or eliminated altogether. For example, the computational model can analyze intensity input of data for a comparative analysis in order to determine with a statistically high degree of certainty, that a particular receptor is bound to a target antigen with specificity.

For example, cluster analysis primarily includes top-down or bottom-up analysis. In addition, massive parallel gene expression monitoring systems and mathematical methods have been developed for utilization with nucleic acid gene array technology. See for example, U.S. Pat. No. 7,197,400, which is incorporated herein by reference. For example, top-down analysis (or best-fit analysis) typically starts with a given number of clusters and proceeds to partition the data into these clusters. In this way, the algorithm randomly assigns centers to each cluster and partitions the nearest data into those clusters. The algorithm iteratively finds new centers of the clusters by averaging over the data in the cluster and reassigning data to new clusters as the centers change. This continues until the centers no longer change.

For another example, bottom-up clustering (or tree clustering) starts by grouping data at the lowest level and builds larger groups by bringing the smaller groups together at the next highest level. In this way, data is clustered together by assigning nearest pairs (according to, for example, information theoretical criteria or regression methods), the algorithm progresses up to the next level of joining the two nearest groups from the prior level as one group. Thus, the number and size of the cluster depends on the level achieved. In this way, the algorithm continues until the analysis of the similarity of the members inside the cluster compared to the difference across clusters indicates cessation.

For another example, SOMS operate as competitive neural networks, and group input data into nearest neighbors based on weights of each neuron receiving input data. The neuron capable of capturing the data results in an update toward the data input. Updating the weights results in a shift in recognition of each neuron toward a center of similar data, thus, the number of neurons provides an estimation of the number of clusters of data.

For another example, principal component analysis includes a stepwise analysis that creates a new component axis at each step where variation is observed in the data. Thus, each component explains the varying bases for the change in the data. In this way, the analysis projects the data into a new space spanned by the principal components.

For another example, iterative independent component analysis reduces input data into components and treats each component as statistically independent from the others. See, for example, U.S. Patent App. Pub. No. 2006/0074566, which is incorporated herein by reference. In this way, data is clustered that allows for maximum correlation of individual members within a group.

In an embodiment, the computer systems described herein include systems including a computer-readable non-transitory medium on which is encoded programming code for analyzing gene expression and/or determining clustering of gene expression, correlation of gene expression, or determining a gene expression profile that is utilized as an antigenic profile for a particular tissue and/or subject. In an embodiment, a gene function is derived from the information obtained from one or more biological assays, including gene expression assays.

Thus, in an embodiment, the antigenic profile includes the qualitative or quantitative characteristics of the antigens present in a particular analysis group, such as a tissue type or disease studied.

Thus, in an embodiment, a method for immunotherapy of a subject comprises determining the qualitative or quantitative differential gene expression between a non-diseased tissue type from one or more tissue samples of two or more non-diseased subjects of a population, and a diseased tissue type from one or more tissue samples of two or more diseased first subjects of a population; deducing the Universal Subject Disease-Specific Antigens pool for the diseased tissue type based on the determination of the differential gene expression; engineering a Universal Subject Disease-Specific Library of multi-specific T cells bearing Chimeric Antigen Receptors each specifically recognize one or more members of the Universal Subject Disease-Specific Antigens pool; obtaining at least one diseased tissue sample from a diseased second subject to be treated, wherein the diseased tissue sample from the diseased second subject to be treated corresponds to the same tissue type as the diseased tissue type from one or more tissue samples of two or more diseased first subjects of a population; analyzing the qualitative or quantitative gene expression of the diseased tissue sample from the diseased second subject to be treated and determining the Universal Subject Disease Specific Antigens pool based on the analysis (thus, examining one or more qualitative or quantitative characteristics of gene expression information, as described herein; comparing the Individual Subject's Disease Specific Antigens pool with the Universal Subject Disease-Specific Antigens pool and determining one or more antigen members in common to both pools; selecting one or more multi-specific T cells bearing Chimeric Antigen Receptors from the Universal Subject Disease-Specific Library effective against the diseased tissue from the diseased second subject to be treated based on the determination of the one or more antigen members in common to both pools; administering a therapeutically effective amount of the selected one or more multi-specific T cells bearing Chimeric Antigen Receptors to the diseased second subject to be treated.

In an embodiment, the non-diseased tissue type from one or more samples of two or more subjects of a population, and the diseased tissue type from one or more tissue samples of two or more diseased second subjects of a population are the same or similar tissue types.

In an embodiment, a method for immunotherapy of a subject comprises obtaining gene sequence information for at least one diseased tissue type antigen from a diseased first subject; comparing the gene sequence information for at least one diseased tissue type antigen from a diseased first subject with one or more previously identified non-diseased tissue type antigens from two or more second subjects, wherein the diseased tissue type from the diseased first subject corresponds to the tissue type of the non-diseased tissue type from the two or more second subjects; and determining a Universal Subject Disease-Specific Antigens pool for a diseased tissue type based on the comparison; engineering a Universal Subject Disease-Specific Library of multi-specific T cells bearing Chimeric Antigen Receptors each specifically recognize one or more members of the Universal Subject Disease-Specific Antigens pool. In an embodiment, the method further includes selecting one or more multi-specific T cells bearing Chimeric Antigen Receptors from the Universal Subject Disease-Specific Library effective against one or more antigens of the diseased tissue from the diseased first subject to be treated based on the determination of the one or more antigen members in common to both pools. In an embodiment, the method further includes administering a therapeutically effective amount of the selected one or more multi-specific T cells bearing Chimeric Antigen Receptors to the diseased first subject to be treated.

In an embodiment, a method for immunotherapy of a subject comprises determining the qualitative or quantitative differential gene expression between a non-diseased tissue type from a subject, and the corresponding diseased tissue type from the subject; deducing the Individual Subject Disease-Specific Antigens pool based on the determination of the differential gene expression; engineering an Individual Subject Disease-Specific Library of multi-specific T cells bearing Chimeric Antigen Receptors each specifically recognize one or more members of the Individual Subject Disease-Specific Antigens pool; selecting one or more multi-specific T cells bearing Chimeric Antigen Receptors from the Individual Subject Disease-Specific Library based on one or more criteria as being the most effective against the diseased tissue type from the subject; administering a therapeutically effective amount of the selected one or more multi-specific T cells bearing Chimeric Antigen Receptors to the subject.

For example, in any of the embodiments described herein, the most effective T CAR cells for a subject is determined based on several factors, including for example, avidity with which the target disease-associated antigen binds the T CAR, the expression level of the target disease-associated antigen on the target diseased cell(s), any clustering of gene expression and the resulting T CAR structural configurations (e.g., a T CAR exhibiting receptor specificity for two different epitopes of the same antigen on a single receptor molecule can be designed in order to have one receptor specificity with increased avidity for one epitope over the other epitope, depending on the avidity or level of expression of the epitope on the target diseased cell), or any of the qualitative or quantitative characteristics described herein (e.g., genetic or mRNA mutations, abnormal post-translational modifications, variant Kd value, methylation/acetylation of nucleic acids, lipid modifications, relative amount of antigens expressed in a diseased tissue versus normal tissue, a cluster expression of several particular antigens in a diseased tissue versus normal tissue, the absence of expression of a normal tissue antigen in a diseased tissue, cell surface density of a single antigen, cell surface concentration of a single antigen, number of copies of an antigen per cell, etc.).

In an embodiment, the functional avidity of the T CAR is engineered in order to increase or decrease the responsiveness of the T CAR to the target disease-associated antigen. For example, higher avidity T CARs are likely to exhibit broader recognition of a target disease-associated epitope, compared to a lower avidity T CAR.

In an embodiment, the recognition domain includes the site at which the T cell receptor physically interacts with the epitope. For example, the avidity of a T cell receptor includes the affinity of the particular epitope with the T cell receptor, but also includes the TCR binding time with the target antigen/MHC complex. At various levels of TCR avidity, calcium mobilization occurs, target cell lysis occurs, or full activation with T cell proliferation occurs. Thus, avidity can be measured by chromium release assay, based on SD50 values (concentration of peptide needed to achieve maximal specific lysis).

In an embodiment, the Kd values of the T CAR cell receptor to antigen binding affinity ranges from about 5.1 to about 6.1 to about 7.1 to about 8.1 to about 9.1 to about 10.1 to about 11.1 to about 12.1 to about 13.1 to about 14.1 to about 15.1 to about 16.1 to about 17.1 to about 18.1 to about 19.1 to about 20.1 nanomolar. In an embodiment, the functional avidity of the T CAR cell receptor to antigen ranges from about 1.0-4.0 log pg/mL for half the maximal inhibition efficiency. In an embodiment, the T CAR cell receptor functional avidity includes about 2.0, about 2.5, or about 3.0 log pg/mL for half the maximal inhibition efficiency.

In an embodiment, the T CAR avidity is inversely proportional to the amount of antigen needed to stimulate a response. Thus, the higher the level of antigen needed, the lower the avidity of the T CAR, whereas if the avidity level of the T CAR is higher, then a lower amount of antigen is needed to stimulate a response. Typically, this means that the higher the Kd value of the T CAR binding to the antigen, the higher the avidity. Thus, in an embodiment, for low levels of diseased-associated antigen(s) expressed on the target diseased cells, the avidity of the T CAR can be modulated to increase the receptor affinity or time contacted with antigen, for overall increased functional avidity. In another embodiment, for high levels of antigen present on the target diseased cell(s), the avidity of the T CAR can be modulated to decrease the overall functional avidity, for example by adjusting the receptor affinity or time contacted with antigen, according to standard practices.

Likewise, for certain embodiments related to various methods described herein, the disease-associated antigens (whether Universal or Individual Subject) are further compared with antigens from one or more vaccinated subjects. Thus, in one embodiment, a comparison is made between diseased and non-diseased tissues (whether from Universal or Individual Subject) and secondarily the output from that first comparison is further compared with vaccinated tissues (from a population or from an individual subject). In one embodiment, a comparison is made directly between diseased and vaccinated tissues (whether Universal or Individual Subject) without first comparing with non-diseased non-vaccinated tissues. In one embodiment, a comparison is made directly between non-diseased and vaccinated tissues (whether Universal or Individual Subject) without first comparing with diseased tissues.

In an embodiment, a method for immunotherapy of a subject comprises: determining the qualitative or quantitative differential gene expression between a non-diseased tissue type from a subject, and the corresponding diseased tissue type from the subject; deducing the Individual Subject Disease-Specific Antigens pool based on the determination of the differential gene expression; engineering an Individual Subject Disease-Specific Library of multi-specific T cells bearing Chimeric Antigen Receptors each specifically recognize one or more members of the Individual Subject Disease-Specific Antigens pool; selecting one or more multi-specific T cells bearing Chimeric Antigen Receptors from the Individual Subject Disease-Specific Library based on one or more criteria as being the most effective against the diseased tissue type from the subject; administering a therapeutically effective amount of the selected one or more multi-specific T cells bearing Chimeric Antigen Receptors to the subject.

In an embodiment, a composition comprises: a Universal Subject Disease-Specific library of engineered T cells including one or more multi-specific Chimeric Antigen Receptors each with selected specificity for two or more epitopes of one or more Universal Subject Disease-Specific Antigens on a single receptor.

In an embodiment, a composition comprises: a Universal Subject Disease-Specific library of engineered T cells including one or more multi-specific Chimeric Antigen Receptor with selected avidity for two or more epitopes of one or more Universal Subject Disease-Specific Antigens on a single receptor. A composition comprises: an Individual Subject Disease-Specific library of engineered T cells including one or more multi-specific Chimeric Antigen Receptor with selected avidity for two or more epitopes of one or more Individual Subject Disease-Specific Antigens on a single receptor.

In an embodiment, a composition comprises: an Individual Subject Disease-Specific library of engineered T cells including one or more multi-specific Chimeric Antigen Receptors each with selected specificity for two or more epitopes of one or more Individual Subject Disease-Specific Antigens on a single receptor.

In an embodiment, a system, comprises: one or more input/output devices having a non-transitory signal bearing medium operable to accept at least one input related to gene expression information from one or more non-diseased tissue antigens from two or more subjects; accept at least one input related to gene expression information from one or more diseased tissue antigens from two or more subjects; compare the input related to gene expression information from one or more non-diseased tissue antigens from two or more subjects with the input related to gene expression information from the corresponding one or more diseased tissue antigens from two or more subjects; generate a differential antigen value based on the comparison; reinitiate accepting at least one input related to gene expression information from one or more non-diseased tissue antigens from two or more subjects, and comparing with the input related to gene expression information from the corresponding gene of the one or more diseased tissue antigens until a differential threshold is satisfied, in an embodiment the differential threshold is based on a pre-determined avidity of the T CAR; and generate a Universal Subject Disease-Specific Antigen dataset for the differential antigen values.

In an embodiment, a system, comprises: one or more input/output devices having a non-transitory signal bearing medium operable to accept at least one input related to gene expression information from one or more non-diseased tissue antigens from a diseased subject to be treated; accept at least one input related to gene expression information from one or more diseased tissue antigens from the diseased subject to be treated; compare the input related to gene expression information from the one or more non-diseased tissue antigens from the diseased subject with the input related to gene expression information from the corresponding one or more diseased tissue antigens from the diseased subject; generate a differential antigen value based on the comparison; reinitiate accepting at least one input related to gene expression information from one or more non-diseased tissue antigens from the diseased subject, and comparing with the input related to gene expression information of the corresponding gene of the one or more diseased tissue antigens until a differential threshold is satisfied, in one embodiment the differential threshold is based on a pre-determined avidity of the T CAR; and generate an Individual Subject Disease-Specific Antigen dataset for the differential antigen values.

In an embodiment, an article of manufacture, comprises: a structure for accepting data related to a subject; a structure for receiving at least one input related to gene expression information from one or more non-diseased tissue antigens from two or more subjects; a structure for receiving at least one input related to gene expression information from one or more diseased tissue antigens from two or more subjects; a structure for comparing the input related to gene expression information from one or more non-diseased tissue antigens from two or more subjects with the input related to gene expression information from the corresponding one or more diseased tissue antigens from two or more subjects; a structure for generating a differential antigen value based on the comparison; a structure for reinitiating accepting at least one input related to gene expression information from one or more non-diseased tissue antigens from two or more subjects, and comparing with the input related to gene expression information from the corresponding gene of the one or more diseased tissue antigens until a differential threshold is satisfied in one embodiment the differential threshold is based on a pre-determined avidity of the T CAR; and a structure for generating a Universal Subject Disease-Specific Antigen dataset for the differential antigen values.

In an embodiment, an article of manufacture, comprises: a structure for accepting data related to a subject; a structure for receiving at least one input related to gene expression information from one or more non-diseased tissue antigens from a diseased subject to be treated; a structure for receiving at least one input related to gene expression information from one or more diseased tissue antigens from the diseased subject to be treated; a structure for comparing the input related to gene expression information from the one or more non-diseased tissue antigens from the diseased subject with the input related to gene expression information from the corresponding one or more diseased tissue antigens from the diseased subject; a structure for generating a differential antigen value based on the comparison; a structure for reinitiating accepting at least one input related to gene expression information from one or more non-diseased tissue antigens from the diseased subject, and comparing with the input related to gene expression information of the corresponding gene of the one or more diseased tissue antigens until a differential threshold is satisfied in one embodiment the differential threshold is based on a pre-determined avidity of the T CAR; and a structure for generating an Individual Subject Disease-Specific Antigen dataset for the differential antigen values.

As used herein, in an embodiment, the differential threshold includes a value, such as a numerical value, and can include a relative value, of one or more qualitative or quantitative gene expression information characteristics. Such qualitative and quantitative gene expression information characteristics have been described herein. As described herein, the differential threshold also includes one or more components related to a predetermined avidity (T CAR affinity, time contacted to antigen, etc.) and in an embodiment the predetermined avidity is based on the functional avidity of the T CAR.

In an embodiment, a method executed on a computing device, comprises accepting data related to a subject; receiving at least one input related to gene expression information from one or more non-diseased tissue antigens from two or more subjects; receiving at least one input related to gene expression information from one or more diseased tissue antigens from two or more subjects; comparing the input related to gene expression information from one or more non-diseased tissue antigens from two or more subjects with the input related to gene expression information from the corresponding one or more diseased tissue antigens from two or more subjects; generating a differential antigen value based on the comparison; reinitiating accepting at least one input related to gene expression information from one or more non-diseased tissue antigens from two or more subjects, and comparing with the input related to gene expression information from the corresponding gene of the one or more diseased tissue antigens until a differential threshold is satisfied in one embodiment the differential threshold is based on a pre-determined avidity of the T CAR; and generating a Universal Subject Disease-Specific Antigen dataset for the differential antigen values.

In an embodiment, a method executed on a computing device, comprises accepting data related to a subject; receiving at least one input related to gene expression information from one or more non-diseased tissue antigens from a diseased subject to be treated; receiving at least one input related to gene expression information from one or more diseased tissue antigens from the diseased subject to be treated; comparing the input related to gene expression information from the one or more non-diseased tissue antigens from the diseased subject with the input related to gene expression information from the corresponding one or more diseased tissue antigens from the diseased subject; generating a differential antigen value based on the comparison; reinitiating accepting at least one input related to gene expression information from one or more non-diseased tissue antigens from the diseased subject, and comparing with the input related to gene expression information of the corresponding gene of the one or more diseased tissue antigens until a differential threshold is satisfied in one embodiment the differential threshold is based on a pre-determined avidity of the T CAR; and generating an Individual Subject Disease-Specific Antigen dataset for the differential antigen values.

In an embodiment, a system, comprises circuitry configured for accepting data related to a subject; circuitry configured for receiving at least one input related to gene expression information from one or more non-diseased tissue antigens from two or more subjects; circuitry configured for receiving at least one input related to gene expression information from one or more diseased tissue antigens from two or more subjects; circuitry configured for comparing the input related to gene expression information from one or more non-diseased tissue antigens from two or more subjects with the input related to gene expression information from the corresponding one or more diseased tissue antigens from two or more subjects; circuitry configured for generating a differential antigen value based on the comparison; circuitry configured for reinitiating accepting at least one input related to gene expression information from one or more non-diseased tissue antigens from two or more subjects, and comparing with the input related to gene expression information from the corresponding gene of the one or more diseased tissue antigens until a differential threshold is satisfied in one embodiment the differential threshold is based on a pre-determined avidity of the T CAR; and circuitry configured for generating a Universal Subject Disease-Specific Antigen dataset for the differential antigen values.

In a method executed on a computing device, comprises circuitry configured for accepting data related to a subject; circuitry configured for receiving at least one input related to gene expression information from one or more non-diseased tissue antigens from a diseased subject to be treated; circuitry configured for receiving at least one input related to gene expression information from one or more diseased tissue antigens from the diseased subject to be treated; circuitry configured for comparing the input related to gene expression information from the one or more non-diseased tissue antigens from the diseased subject with the input related to gene expression information from the corresponding one or more diseased tissue antigens from the diseased subject; circuitry configured for generating a differential antigen value based on the comparison; circuitry configured for reinitiating accepting at least one input related to gene expression information from one or more non-diseased tissue antigens from the diseased subject, and comparing with the input related to gene expression information of the corresponding gene of the one or more diseased tissue antigens until a differential threshold is satisfied in one embodiment the differential threshold is based on a pre-determined avidity of the T CAR; and circuitry configured for generating an Individual Subject Disease-Specific Antigen dataset for the differential antigen values.

As described herein, Disease-Specific Antigens (whether Universal or Individual) includes particular antigens that originate from viruses (in diseases caused by viruses), and also includes antigens that are not particular to any specific histology or tissue but instead are common to disease, such as tumors. In an embodiment, the Disease-Associated Antigens are protein structures that contain mutation sin their sequence or are exhibit aberrant expression on tumor or diseased tissue versus normal tissue.

For example, some Disease-Specific Antigens include, but are not limited to tumor-associated antigens such as EBNA-3, E6, E7, carcinoembryonic antigen (CEA), her-2/neu, Muc-1, MART-1, gp100, tyrosinase, p53, beta-catenin, CDK4, alphafetoprotein, ras, and others. For example, some Disease-Specific Antigens include, but are not limited to tumor-associated antigens such as O antigens (lipopolysaccharide molecules from bacterial membranes), H antigens (components of flagella), K antigens (polysaccharides from bacterial capsules), or "clumping factors" (molecules bound to the outer surface causing agglutination. For example, some Disease-Specific Antigens include, but are not limited to, viral envelope proteins or other viral proteins.

As described in FIG. 1A, and described in more detail in the Prophetic Examples section herein, construction of a Universal Memory T cell Line is conducted, for example, by engineering T memory cells (Tcm) at the Cre/lox recombination site, as drawn 100, by standard homologous recombination techniques. The nucleic acid molecule is placed into the host cell such that the innate T cell receptor constant region alpha chain is disrupted, 110, thereby prohibiting innate T cell receptor formation in the host cell. The engineered cells are selected for CD3(−), CD8+ 120.

Figure 1B:
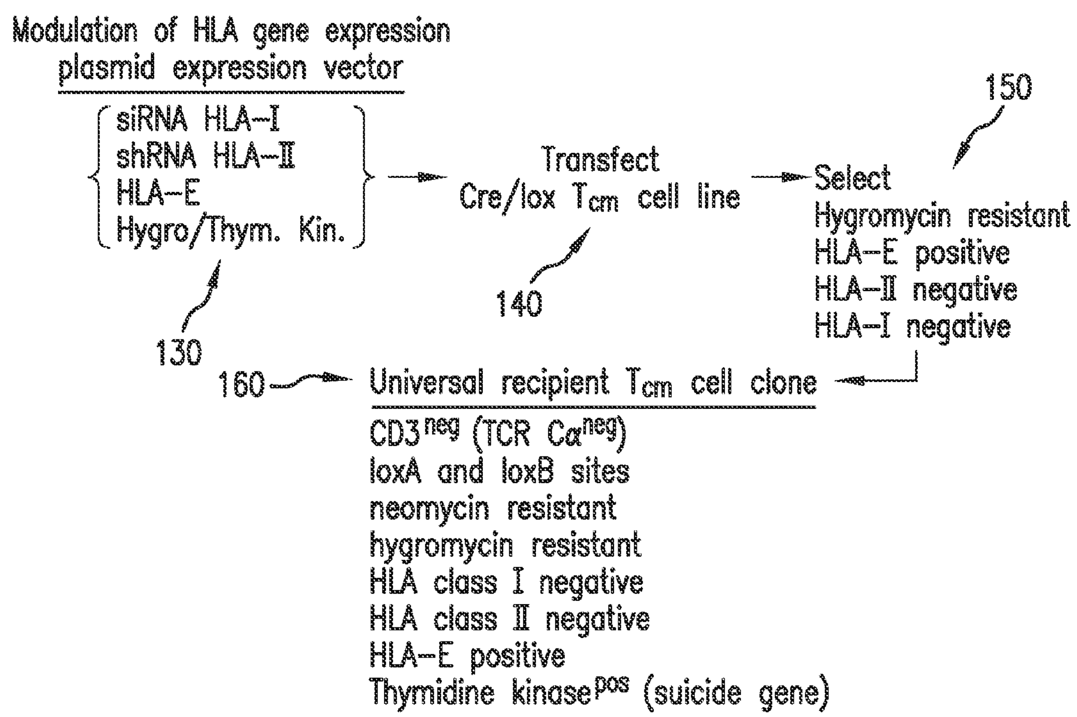
FIG. 1B is a partial view of an embodiment related to engineering an artificial T cell line.

As described in FIG. 1B, HLA gene expression is optionally altered such that innate host cell NK and T cell elimination of the engineered T CAR cells is reduced or eliminated. For example, silencing RNA (siRNA or shRNA) are utilized to prevent expression of HLA I and/or HLA II, while HLA-E is engineered into the vector, as well as selection markers (e.g., hygromycin, thymidine kinase) 130. Next, the plasmid expression vector is transfected into the Cre/lox Tcm cell line as described 140 and positive clones selected 150 based on the selection criteria. The resulting Tcm cell clones are Universal Recipient Tcm cell lines as described 160.

Figure 2A:
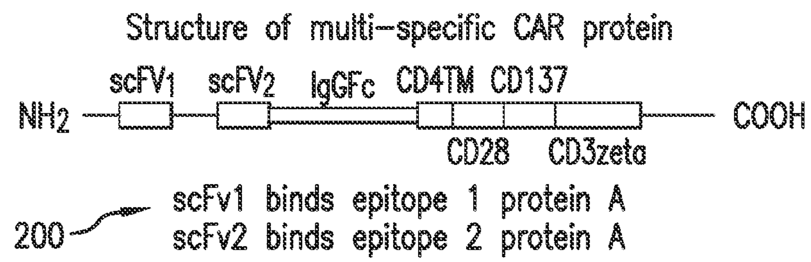
FIG. 2A is a partial view of an embodiment related to constructing a multi-specific chimeric antigen receptor.

As described in FIG. 2A, the structure of a multi-specific CAR, for example, includes at least two scFVs each specific to two different epitopes of the same antigen, or two different antigens 200. The artificially engineered multi-specific CAR is utilized for site-specific integration into the Universal recipient Tcm cell line, as described herein. For example, at the lox sites of the targeting vector 210, 220 with Cre recombinase expression vector 230 and CMV promoter, with DHFR selectable marker 240.

Figure 2B:
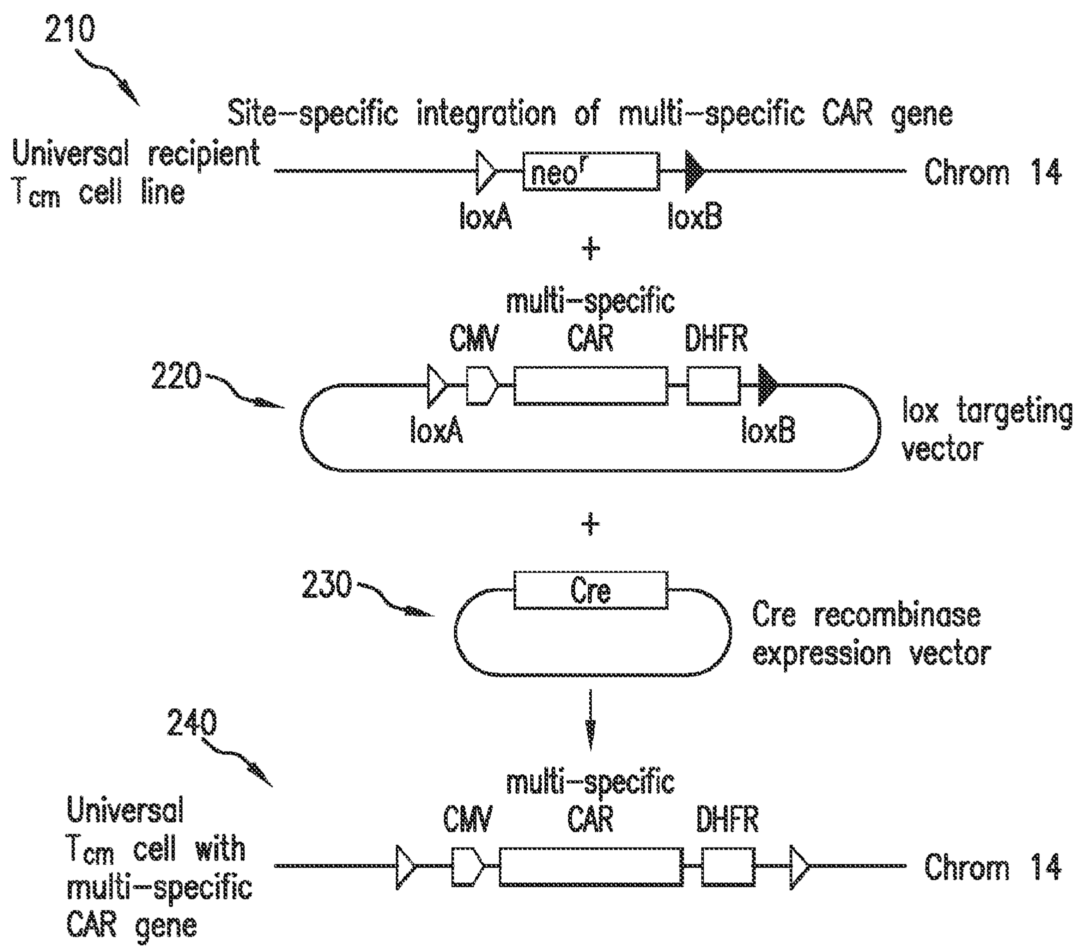
FIG. 2B is a partial view of an embodiment related to constructing a multi-specific chimeric antigen receptor.
Figure 2C:
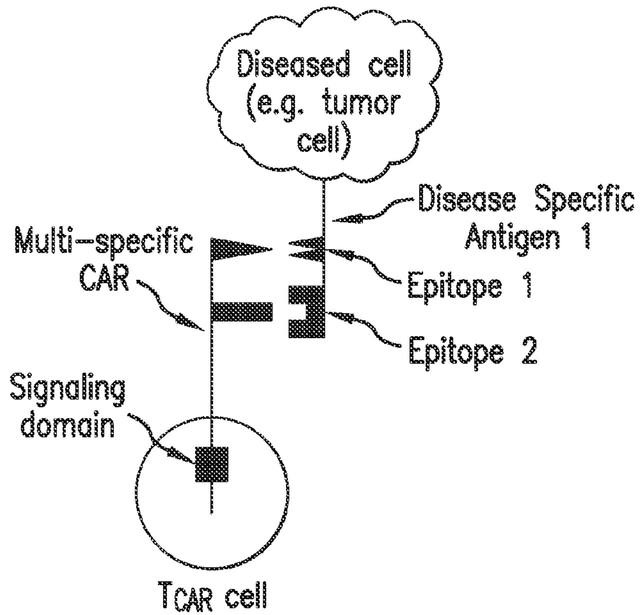
FIG. 2C is a partial view of an embodiment related to constructing a multi-specific chimeric antigen receptor.

As described in FIG. 2C, in an embodiment, a multi-specific T CAR recognizes two or more different epitopes of one antigen. That is, a T CAR expressed as a single molecule includes multi-specific epitope recognition. Having recognition of two or more epitopes of a single antigen provides for a greater likelihood of the T CAR contacting the target antigen. Moreover, since the multi-specific epitope recognition sites are both on a single molecule, there is a greater chance of physical contact with the target antigen. Thus, FIG. 2C illustrates a diseased cell (e.g., tumor cell) exhibiting multiple epitopes of a particular antigen (Epitope 1 and Epitope 2 of Disease-Specific Antigen 1) that are specifically recognized by the multi-specific T CAR expressed on the T cell (also illustrated is the internal T CAR signaling domain for activation of the T CAR upon binding with the cognate antigens).

Figure 2D:
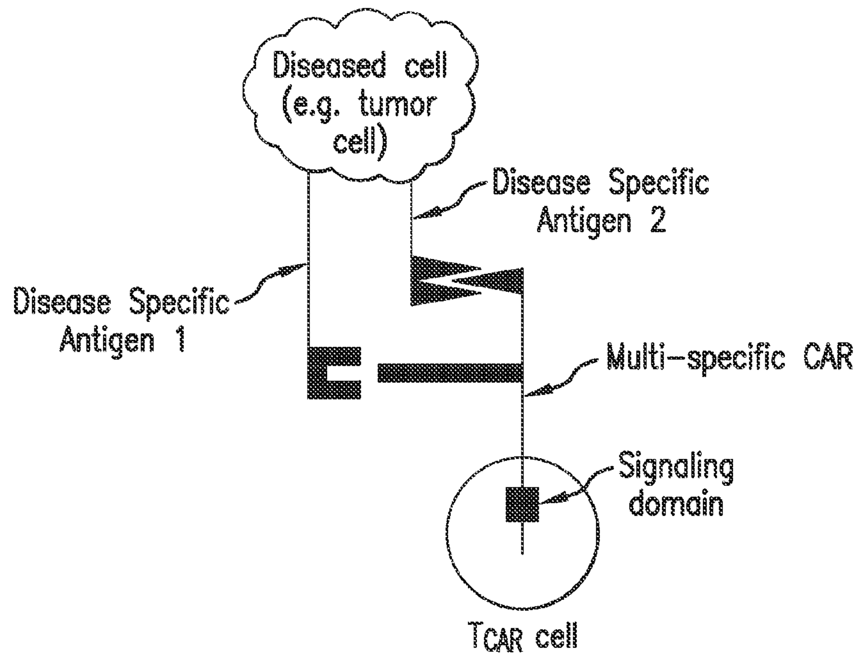
FIG. 2D is a partial view of an embodiment related to constructing a multi-specific chimeric antigen receptor.

As described in FIG. 2D, in an embodiment, a multi-specific T CAR recognizes two different antigens. That is, a T CAR expressed as a single molecule includes multi-specific antigen recognition. Having recognition of two or more different antigens increases the likelihood of the T CAR contacting the target antigens. Furthermore, since the multi-specific antigen recognition sites are both on a single molecule, there is a great chance of physical contact with the target antigen (vs. having separate receptors for each antigen). Thus, FIG. 2D illustrates a diseased cell (e.g., tumor cell) exhibiting multiple antigens (Disease-Specific Antigen 1 and Disease-Specific Antigen 2) that are specifically recognized by the multi-specific T CAR expressed on the T cell (also illustrated is the internal T CAR signaling domain for activation of the T cell upon binding of the T CAR with the cognate antigens).

Figure 3:
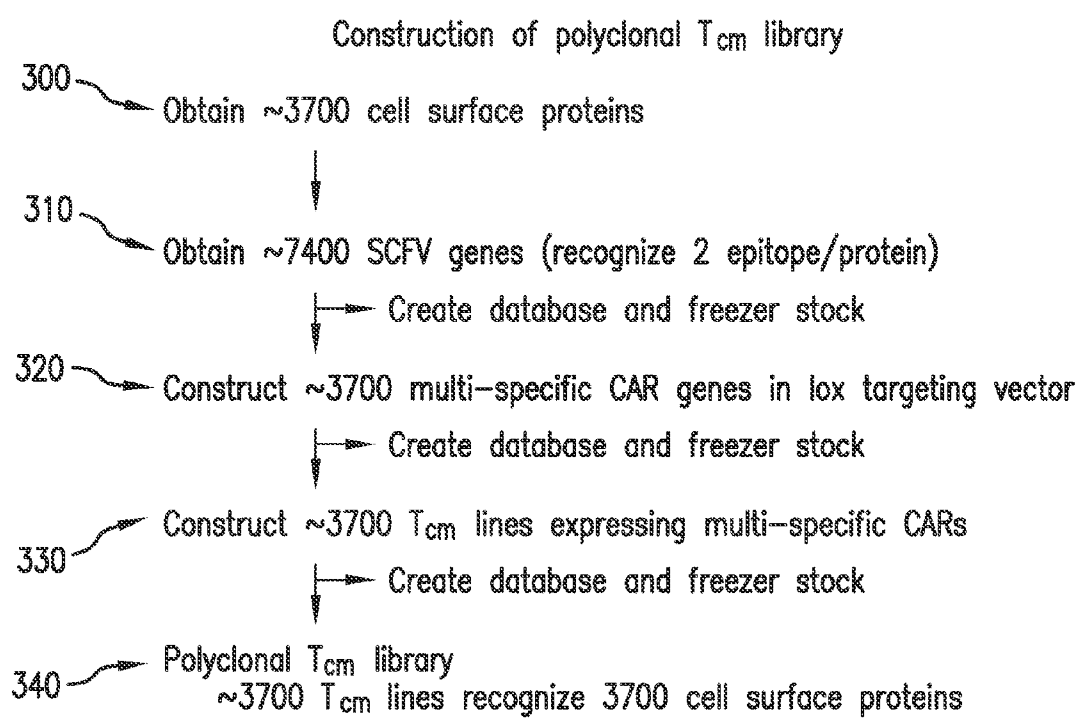
FIG. 3 is a partial view of an embodiment related to engineering an artificial T cell line, and computer systems thereof.

As described in FIG. 3, Construction of a polyclonal Tcm library is constructed, for example, by obtaining the listing of all currently identified human cell surface antigens 300, and screening the surface antigens for specific receptor-antigen pairs with scFv genes 310. The parameters for screening are set according to the desired outcome, and in one embodiment two scFvs that specifically recognize two different epitopes on a single antigen are selected 310. From this selection process, a database is created with the sequences, and a freezer stock maintained 310. Next, multi-specific CAR genes are constructed in the lox targeting vector as described herein, for all of the currently identified human cell surface antigens (~3700), and a database and freezer stock maintained 320. The multi-specific CAR vectors are transfected into the recipient Tcm cell line, resulting in Tcm cell lines expressing multi-specific CARs, and a database and freezer stock are maintained 330, producing a polyclonal Tcm library with bi-specific recognition of approximately 3700 human cell surface antigens 340.

Figure 4:
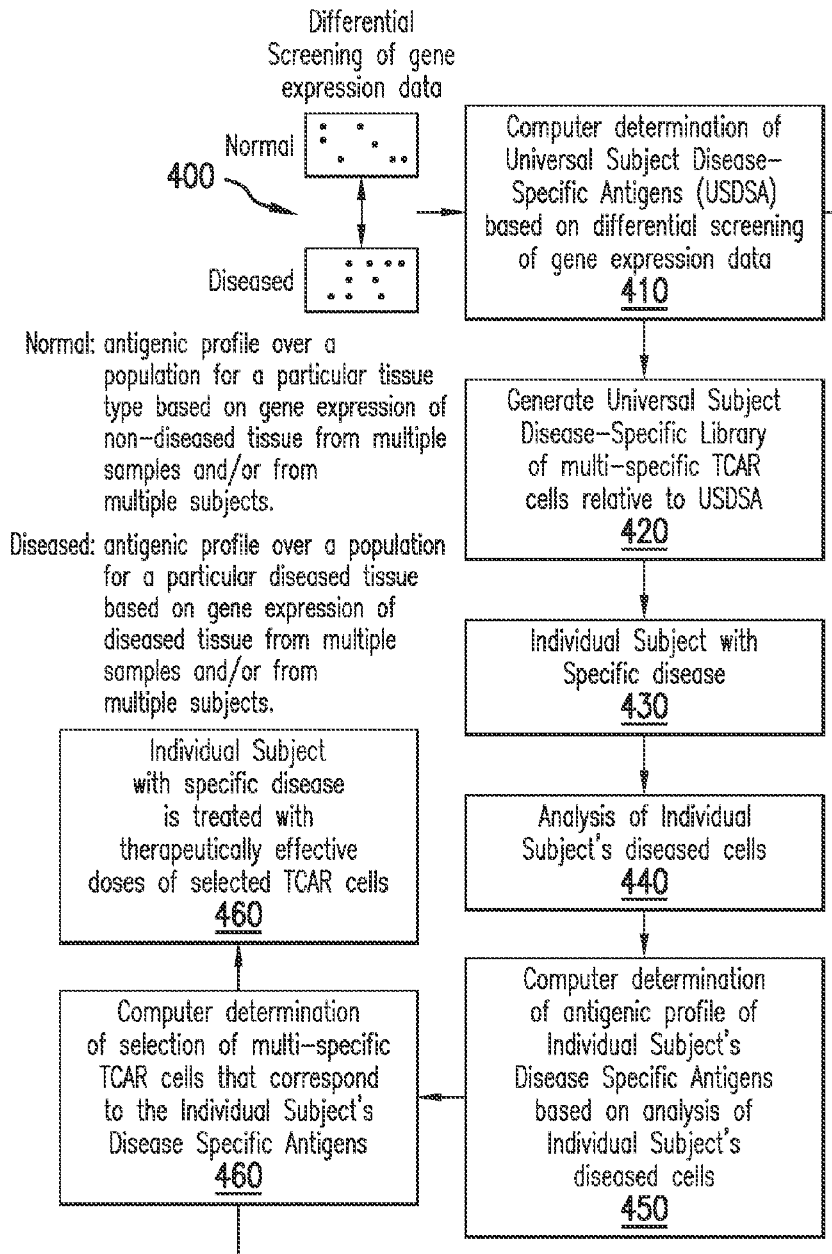
FIG. 4 is a partial view of an embodiment related to engineering an artificial T cell line, and computer systems thereof.
Figure 4:
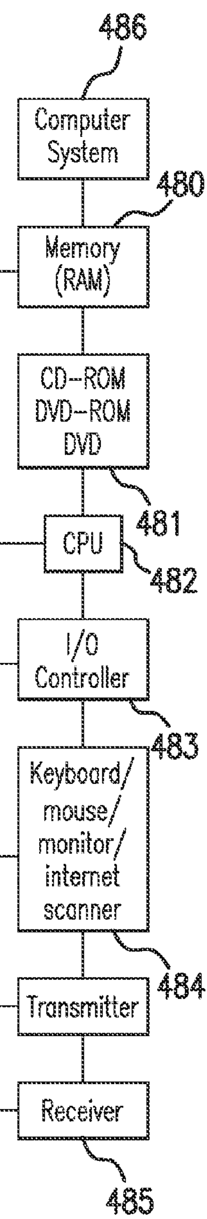

As described in FIG. 4, a Universal Subject Disease-Specific library and Methods of Making and Administering are included. For example, an initial differential screening of gene expression data 400 of normal tissue cell surface proteins (antigenic profile over a population for a particular tissue type based on gene expression of non-diseased tissue from multiple samples and/or from multiple subjects) compared with diseased tissue antigens (antigenic profile over a population for a particular diseased tissue based on gene expression of diseased tissue from multiple samples and/or from multiple subjects) is utilized for a computer determination of Population Disease-Specific Antigens (PDSA) based on the differential screening 410. Next, a library is generated for the Universal Subject Disease-Specific Library of multi-specific (including bispecific) T CAR cells effective against the PDSA 420. Next, an individual subject with a specific disease is addressed 430. A biopsy or other cell or fluid sample is obtained from the diseased subject and analysis of the sample is performed 440.

Next, a computer determination of the antigenic profile of the Individual Subject's Disease Specific Antigens is made based on the analysis of the Individual Subject's diseased cells 450. Next, a computer determination of the selection of which multi-specific T CAR cells correspond to the Individual Subject's Disease-Specific Antigens is conducted 460.

Finally, the Individual Subject with specific disease is treated with a therapeutically effective dose of T CAR cells specifically selected for the subject, based on the analysis of the individual subject's diseased cells in the context of the Universal Subject Disease Specific Library 470. In this way, a library can be constructed for any particular tissue type or disease type. In an embodiment, several libraries are established for various stages of disease progression (e.g., metastasis, or chronic disease such as Alzheimer's or multiple sclerosis).

Regarding the computer systems utilized for the computer determinations of various aspects described herein, FIG. 4 also describes a flow of information in a system including the computer software and hardware utilized herein. For example, a computer device or system 486 such as appended to the flow chart of FIG. 4, can be employed. As shown, a CPU 482 or other computer processor includes, for example, digital logic processors capable of processing input, executing algorithms, and generating output as needed in response to the inputs received from an input device (e.g., keyboard, mouse, monitor, internet, scanner, etc. 484). Such processors may include a microprocessor, such as ASIC, and may include or be in communication with media, such as non-transitory media, including computer-readable media which stores instructions that, when executed by the processor, cause the processor to perform the steps described herein. In an embodiment, data is stored or collected by memory (e.g., RAM) 480 includes for example, memory storage device, system memory, or cache memory, and can be stored on media, for example, CD-ROM, DVD-ROM, or DVD, floppy disc, etc. 481. In an embodiment, an I/O controller 483 is utilized to manage the data communications of the computer system. The I/O controller 483 includes any of a variety of devices for accepting and processing information from a user (e.g. machine or human; local or remote), and can include for example, modem cards, wireless cards, network interface cards, sound cards, or other types of controllers for any of a variety of standard input devices. In an embodiment, an output controller of the I/O controller 483 includes, for example, a display device for presenting information to a user (e.g., human or machine; remote or local), and any of the various iterations includes network or other types of remote communication. In an embodiment, a transmitter 485 and/or receiver 485 to transmit or receive data from one database to another or from one central data processing facility to one or more user facilities. In an embodiment, a transmitter and/or receiver includes circuitry configured for transmitting or receiving information, respectively, as well as any corresponding software. In an embodiment, a transmitter and/or receiver includes an antenna, Bluetooth™, or other wireless device, as well as any corresponding software.

Figure 5:
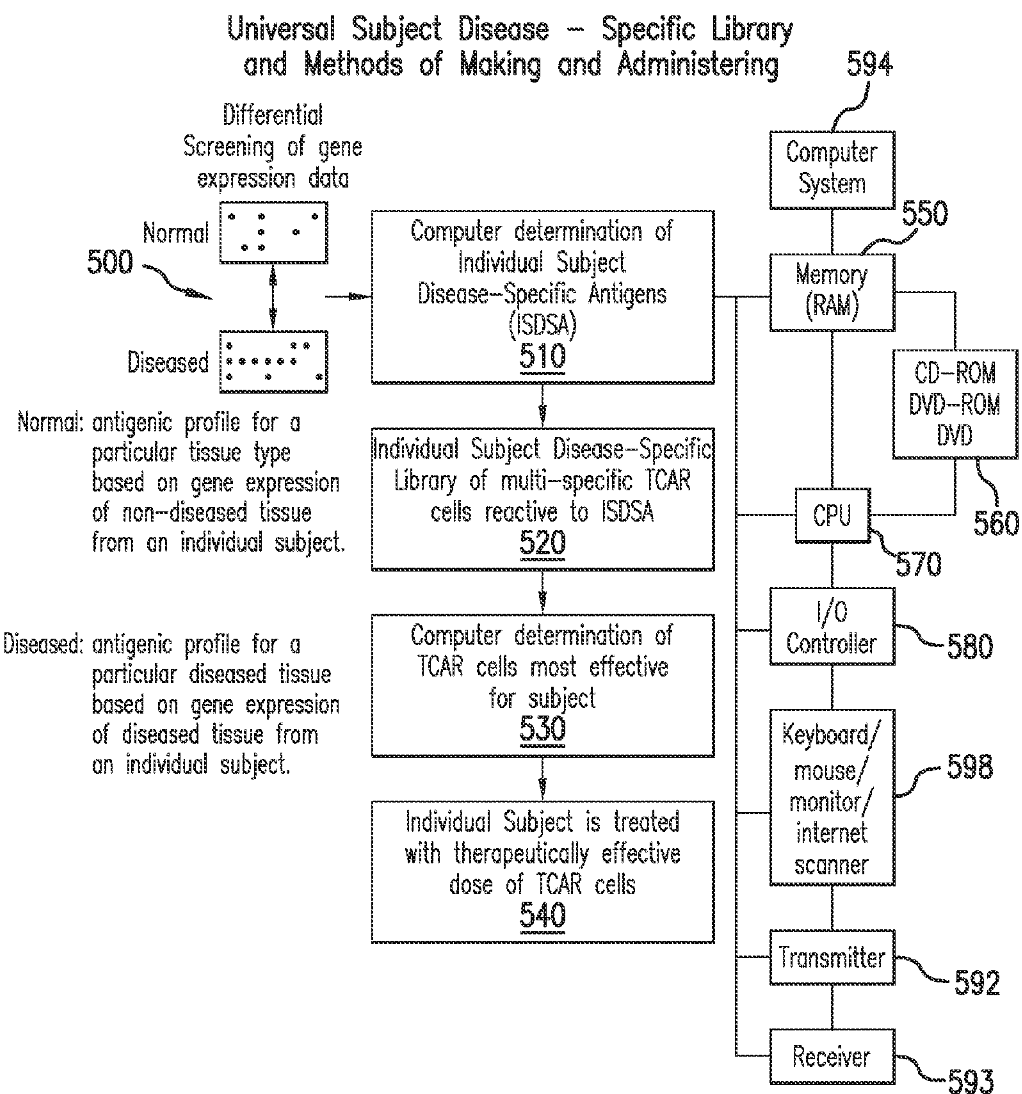
FIG. 5 is a partial view of an embodiment related to engineering an artificial T cell line and computer systems thereof.

As described in FIG. 5, an Individual Subject Disease-Specific library and Methods of Making and Administering are included. For example, an initial differential screening of gene expression data 500 of normal tissue cell surface proteins (antigenic profile for a particular tissue type based on gene expression of non-diseased tissue from an individual subject) compared with diseased tissue antigens (antigenic profile for a particular tissue based on gene expression of diseased tissue from an individual subject) is utilized for a computer determination of Individual Subject Disease-Specific Antigens (ISDSA) based on the differential screening 510. Next, a library is generated for the Individual Subject Disease-Specific Library of multi-specific (including bispecific) T CAR cells reactive to the ISDSA 520. Next, computer determination and selection of the T CAR cells most effective for the subject based on the multi-specificity of particular antigens is conducted 530. Finally, the individual subject is treated with a therapeutically effective dose of T CAR cells 540.

Regarding the computer systems utilized for the computer determinations of various aspects described herein, in an embodiment, one or more logic devices are included. In an embodiment, one or more computing devices are included.

As illustrated in FIG. 5 also describes a flow of information in a system including the computer software and hardware utilized herein. For example, a computer device or system 594 such as appended to the flow chart of FIG. 5, can be employed. As shown, a CPU 570 or other computer processor includes, for example, digital logic processors capable of processing input, executing algorithms, and generating output as needed in response to the inputs received from an input device (e.g., keyboard, mouse, monitor, internet, scanner, etc. 590). Such processors may include a microprocessor, such as ASIC, and may include or be in communication with media, such as non-transitory media, including computer-readable media which stores instructions that, when executed by the processor, cause the processor to perform the steps described herein. In an embodiment, data is stored or collected by memory (e.g., RAM) 550 includes for example, memory storage device, system memory, or cache memory, and can be stored on media, for example, CD-ROM, DVD-ROM, or DVD, floppy disc, etc. 560. In an embodiment, an I/O controller 580 is utilized to manage the data communications of the computer system. The I/O controller 580 includes any of a variety of devices for accepting and processing information from a user (e.g. machine or human; local or remote), and can include for example, modem cards, wireless cards, network interface cards, sound cards, or other types of controllers for any of a variety of standard input devices. In an embodiment, an output controller of the I/O controller 580 includes, for example, a display device for presenting information to a user (e.g., human or machine; remote or local), and any of the various iterations includes network or other types of remote communication. In an embodiment, a transmitter 592 and/or receiver 593 to transmit or receive data from one database to another or from one central data processing facility to one or more user facilities. In an embodiment, a transmitter and/or receiver includes circuitry configured for transmitting or receiving information, respectively, as well as any corresponding software. In an embodiment, a transmitter and/or receiver includes an antenna, Bluetooth™, or other wireless device, as well as any corresponding software.

Figure 6:
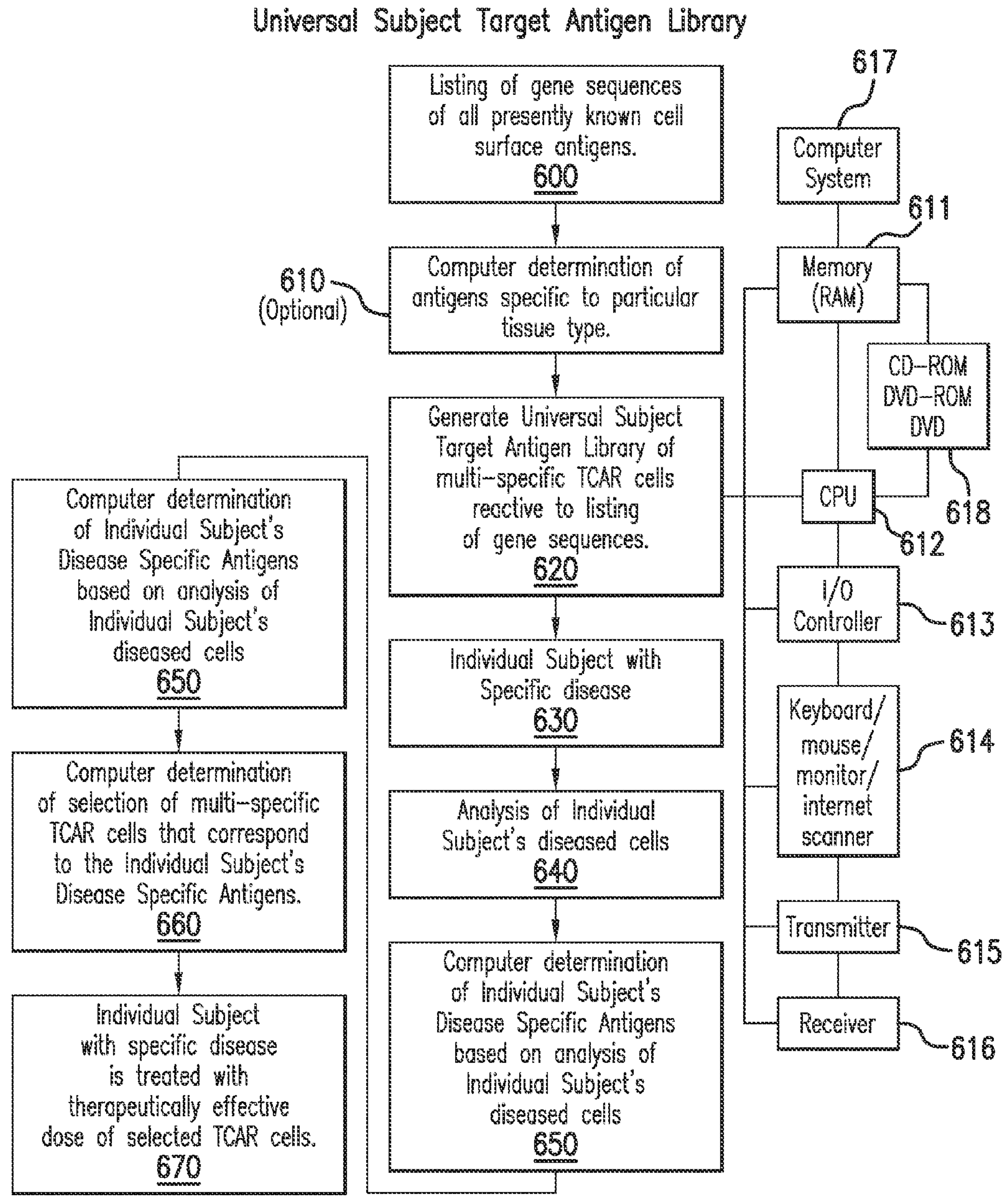
FIG. 6 is a partial view of an embodiment related to engineering an artificial T cell line and computer systems thereof.

As described in FIG. 6, in an embodiment, a listing of gene sequences of all presently identified human cell surface antigens 600 is utilized for a computer determination of antigens specific to a particular tissue type (optional step) 610. Next, a Universal Subject Disease Specific Antigen Library of multi-specific T CAR cells reactive to the listing of gene sequences is generated 620, and an individual subject with a specific disease is addressed 630. Next, a biopsy or other cell or fluid sample is obtained from the individual subject at the disease site and analysis of the individual subject's diseased cells is conducted 640. Next, a computer determination of the Individual Subject's Disease Specific Antigens (ISDSA) based on the analysis of the individual subject's diseased cells 650. Next, computer determination of selection of multi-specific T CAR cells are conducted that correspond to the Individual Subject's Disease-Specific Antigens (ISDSA) 660. Finally, the individual subject with specific disease is treated with a therapeutically effective dose of selected T CAR cells based on the analysis of the individual subject's disease-specific antigens in light of the library.

Regarding the computer systems utilized for the computer determinations of various aspects described herein, FIG. 6 also describes a flow of information in a system including the computer software and hardware utilized herein. For example, a computer device or system 617 such as appended to the flow chart of FIG. 6, can be employed. As shown, a CPU 612 or other computer processor includes, for example, digital logic processors capable of processing input, executing algorithms, and generating output as needed in response to the inputs received from an input device (e.g., keyboard, mouse, monitor, internet, scanner, etc. 614). Such processors may include a microprocessor, such as ASIC, and may include or be in communication with media, such as non-transitory media, including computer-readable media which stores instructions that, when executed by the processor, cause the processor to perform the steps described herein. In an embodiment, data is stored or collected by memory (e.g., RAM) 611 includes for example, memory storage device, system memory, or cache memory, and can be stored on media, for example, CD-ROM, DVD-ROM, or DVD, floppy disc, etc. 618. In an embodiment, an I/O controller 613 is utilized to manage the data communications of the computer system. The I/O controller 613 includes any of a variety of devices for accepting and processing information from a user (e.g. machine or human; local or remote), and can include for example, modem cards, wireless cards, network interface cards, sound cards, or other types of controllers for any of a variety of standard input devices. In an embodiment, an output controller of the I/O controller 613 includes, for example, a display device for presenting information to a user (e.g., human or machine; remote or local), and any of the various iterations includes network or other types of remote communication. In an embodiment, a transmitter 615 and/or receiver 616 to transmit or receive data from one database to another or from one central data processing facility to one or more user facilities. In an embodiment, a transmitter and/or receiver includes circuitry configured for transmitting or receiving information, respectively, as well as any corresponding software. In an embodiment, a transmitter and/or receiver includes an antenna, Bluetooth™, or other wireless device, as well as any corresponding software.

In an embodiment, the computing system includes, for example, at least one of a notebook computer, a work station, a personal data device, a desktop computer, a cluster of processors, a cluster of servers, a cloud computing center, a mobile telephone, or other computing device.

In an embodiment, a computer or other processing unit is configured to receive or transmit information relating to receipt of information from a subject by, for example, a USB cable or wireless network. In an embodiment, a computer or other processing unit is configured for receiving or storing information.

In an embodiment, the computer or other processing unit is configured to allow input or output of additional information or sharing of information, for example, with a subject's personal medical file or population medical health records. That is, in an embodiment, input or output of information related to two or more subjects or an individual subject can be shared with public health databases, or transferred to a subject's specific medical record (including electronic records). In an embodiment, the information shared with public health databases is anonymized such that identifying information related to the subject has been removed, altered, or encrypted.

PROPHETIC EXAMPLES

Example 1

Construction Of a Universal Recipient T Cell Clone for Efficient CAR Gene Integration and T Cell Library Construction A cloned universal recipient T cell with a targeted recombination site for site-specific introduction of chimeric antigen receptor (CAR) genes is constructed from human cytotoxic T lymphocytes (CTL) using a Cre/lox recombination system. For example, to create a recipient T cell clone, central memory T cells (Tcm) are purified from human peripheral blood mononuclear cells (PBMNC) by cell sorting using fluorochrome-conjugated antibodies for CD8 and CD62L (antibodies and cell sorter available from BD Biosciences, San Jose, Calif.). Methods to purify and propagate Tcm in vitro are described (see e.g., Berger et al., *J. Clin. Investigation* 118: 294-305, 2008 which is incorporated herein by reference). To create a targeted recombination site in the Tcm, they are transfected with a targeting site vector containing DNA sequences homologous to regions flanking the gene encoding the constant region of the T cell receptor alpha chain (TCR Cα), and recombination sites for the Cre/lox recombination system. See FIG. 1A.

Methods and vectors using homologous recombination to integrate DNA constructs at specific chromosomal sites in mammalian cells are described (see e.g., U.S. Pat. No. 5,202,238 issued to Fell Jr. et al. on Apr. 13, 1993 which is incorporated herein by reference). Also, DNAs and methods to create cells with mutant loxP sites that promote site-specific integration of exogenous genes are described (see e.g., Araki et al., Comparative analysis of right element mutant lox sites on recombination efficiency in embryonic stem cells, *BMC Biotechnology* 10: 29, 2010; Araki et al., Targeted integration of DNA using mutant lox sites in embryonic stem cells, *Nucleic Acids Research* 25: 868-872, 1997; U.S. Pat. No. 6,130,364 issued to Jakobovits et al. on Oct. 10, 2000 and U.S. Pat. No. 5,928,914 issued to Leboulch et al. on Jul. 27, 1999 which are incorporated herein by reference). Tcm with the targeting site vector DNA, including the lox recombination site, inserted in the TCR Cα gene are isolated by cell sorting for $CD8^+$, $CD3^{neg}$ cells and selecting for drug-resistance (conferred by a drug resistance marker, e.g., neomycin resistance gene (neo) on the targeting DNA construct). See FIG. 1A 120. See e.g., Araki et al., 1997, *Ibid*. and U.S. Patent App. Pub. No. 2012/0060230 by Collingwood et al. published on Mar. 8, 2012 which are incorporated herein by reference. $CD3^{neg}$ Tcm cells with a lox recombination site disrupting the TCRα gene are expanded in vitro and subjected to additional recombinant DNA modifications to prevent recognition and killing of the universal recipient T cell clone by host T cells and NK cells.

To create a universal recipient T cell clone suitable for use in subjects with different HLA haplotypes the $CD3^{neg}$ Tcm cells bearing a lox recombination site (see above) are genetically modified to prevent recognition by host (i.e., patient) T cells and NK cells. Expression of HLA Class I and Class II genes is down-regulated to prevent T cell recognition of the universal Tcm cells. See FIG. 1B 130. For example, short hairpin RNAs (shRNA) which bind to mRNA encoding Class I (HLA-A, -B, -C) and Class II (HLA-DR, -DQ, -DP) and prevent their translation into protein may be used to down-regulate HLA protein expression. Various expression vectors and shRNA nucleotide sequences to produce shRNAs in T cells that inhibit HLA protein expression can be utilized with various embodiments described herein (see e.g., U.S. Patent Application No. 2007/0036773 by Cooper et al. published on Feb. 15, 2007 which is incorporated herein by reference). For example a 58 nucleotide shRNA which inhibits HLA-A, -B and -C alpha chain expression may be encoded in a plasmid vector containing a selectable marker (see e.g., U.S. Patent Appl. No. 2007/0036773, *Ibid*.).

To prevent cytolytic attack by NK cells a nonclassical HLA antigen, HLA-E, is expressed on the Tcm cell surface using an expression construct for HLA-E. A DNA construct encoding HLA-E under the control of a constitutive promoter element and a selection/suicide gene, hygromycin phosphotransferase/thymidine kinase gene (Hy/TK) are described (see e.g., U.S. Patent Application No. 2007/0036773, *Ibid*.). The Hy/TK gene may be used for positive (Hy) or negative (TK) selection, followed by transfection of Cre/lox Tcm cell line 140. Thymidine kinase serves as a suicide gene in the Tcm cells in the event they need to be eliminated in vivo. Administration of gancyclovir to Tcm cells expressing TK results in the production of toxic metabolites which kill the Tcm cells. Universal Tcm cells which are: $CD3^{neg}$, HLA Class $I^{neg}$, HLA Class $II^{neg}$, resistant to G418 (i.e. $neo^r$), resistant to hygromycin, and express HLA-E are selected and cloned 150. See FIG. 1B. The universal recipient Tcm cells are used to create Tcm expressing CAR genes through a process of site-specific integration, as described in FIG. 1B 160.

Example 2

Efficient Site-Specific Integration of CAR Genes in the Universal Recipient Tcm Cell Line As illustrated in FIGS. 1 A, 1 B, 2A, and 2B, multi-specific (at least two specific receptor recognition sites on the same CAR) CAR genes are integrated at the lox recombination site constructed in the universal recipient Tcm cell clone at the TCR Cα locus on chromosome 14 (see FIGS. 1A and 1B). Cultures of the $CD3^{neg}$, $HLA^{neg}$, $HLA\text{-}E^+$ Tcm cells with a lox recombination site are transfected with a lox targeting vector which contains: lox recombination sites, a multi-specific CAR gene and a selection marker gene, e.g., dihydrofolate reductase (DHFR) which confers resistance to a cytotoxic drug, methotrexate (MTX). See FIG. 2B. The genes for CAR and DHFR are controlled by constitutive promoters, e.g., EF-1α and CMV promoters. Universal recipient Tcm cells are cotransfected with a vector which directs transient expression of the Cre recombinase 100 (see e.g., U.S. Pat. No. 6,130,364, *Ibid*.). Cre-mediated recombination between the lox sites in the Tcm cell and the lox targeting vector results in integration of the multi-specific CAR gene and DHFR at the TCRα locus on chromosome 14 110. The transfected Tcm cells are selected in MTX-containing medium and selected for expression of the multi-specific CAR protein using flow cytometry. For example, fluorescent antibodies specific for human IgG Fc hinge are used to detect Tcm cells expressing a CAR gene. Site specific integration in approximately 16% of the recipient cells may be observed (see e.g., Araki et al., 1997, *Ibid.*)

Example 3

Construction of Polyclonal T Cell Library Expressing CARs Recognizing Currently Identified Human Cell Surface Proteins A library of CAR genes is constructed to specifically recognize each of all currently identified human cell surface antigens. See FIG. 3. CARs are constructed with single chain antibodies providing specific binding to cell surface antigens. A comprehensive list of 3,702 human transmembrane proteins derived from the DNA sequence of the human genome 300 (see e.g., Cunha, et al., *Proc. Natl. Acad. Sci. USA* 106: 16752-16757, 2009 which is incorporated herein by reference) is targeted by the CAR library.

Single chain variable region fragments (SCFv) which bind to each cell surface antigen (based on the known sequences thereof) may be identified by screening phage display libraries comprised of human SCFv 310. For example, bacteriophage expressing a library of approximately $3\times10^8$ SCFv may be screened for binding to cell surface antigens (see e.g., De Kruif et al., *Proc. Natl. Acad. Sci. USA* 92: 3938-3942, 1995 and Rader et al., *Current Opinion Biotechnology* 8: 503-508, 1997 which are incorporated herein by reference). Cell surface antigens to screen the SCFv phage library may be made using recombinant DNA methods to synthesize the corresponding genes and express them in vitro (see e.g., Sambrook and Russell, 2001, *Molecular Cloning,* 3rd Ed., Cold Spring Harbor Laboratory Press, Cold Spring Harbor, N.Y. which is incorporated herein by reference).

Alternatively, antibodies and SCFv recognizing cell surface antigens may be obtained from an online database of antibodies against human protein targets (see e.g., Antibodypedia Nature database online at: antibodypedia dot com.) The identification numbers and locations of the bacteriophage-SCFv clones and the corresponding cell surface antigens they recognize are stored in a searchable computer database.

The SCFv clones are stored as bacteriophage frozen stocks which can be used to amplify the DNA sequences encoding the SCFvs and incorporate them in a CAR. Methods to amplify DNA sequences and to construct CAR genes are described (see e.g., U.S. Pat. No. 7,354,762 issued to Jensen on Apr. 8, 2008 which is incorporated herein by reference). For example, a gene encoding a CAR may contain: a SCFv, a human IgG1 Fc hinge domain, a CD4 transmembrane domain, and portions from the cytoplasmic domains of CD28, CD137 and CD3 zeta chain (see e.g., Park et al. *Trends in Biotechnology* 29: 550-557, 2011 which is incorporated herein by reference).

To create multi-specific CAR genes a single SCFv is replaced by two SCFv in tandem. See FIG. 2A 200. Conventional methods and peptide sequences to construct multi-specific antigen receptors are used (see e.g., Mack et al., *Proc. Natl. Acad. Sci. USA* 92: 7021-7025, 1995 which is incorporated herein by reference).

A library of CAR genes is created in a lox targeting vector with specificities for each of all currently identified cell surface antigens using recombinant DNA methods (see e.g., Sambrook and Russell, *Ibid.*) A library of multi-specific CAR genes is created by pairing SCFvs specific for surface antigens. For example, two different scFvs which recognize two different epitopes from a single cell surface protein may be paired to create a multi-specific CAR. See FIG. 2A 200. Alternatively, scFvs recognizing two different cell surface proteins may be paired to construct a multi-specific CAR. A searchable database is created with records for each multi-specific CAR vector including: antigen specificities, corresponding SCFvs and the freezer location of DNA stocks for each lox targeting vector.

A polyclonal Tcm cell library is constructed using the universal recipient Tcm cells and the CAR gene library created in the lox targeting vector. See FIG. 2B 210-230, and FIG. 3 330-340. Individual CAR genes are transfected into aliquots of approximately $10^6$ recipient cells in individual wells of a multiwell plate (50-100 wells) and placed in selective media containing MTX. See FIG. 2B 240. Surviving Tcm cells are screened using flow cytometry to identify cells expressing CAR on their cell surface. For example, fluorescent antibodies recognizing the IgG1 hinge Fc segment on the CARs may be used for flow analysis. Systems and methods for high throughput mammalian cell transfection and selection are described (see e.g., Muller-Hartmann et al., *Expert Opin. Drug Discov.* 2: 1453-1465, 2007 which is incorporated herein by reference). A searchable database is created with records for each Tcm line detailing the location of the Tcm cell stock, the multi-specific CAR expressed, the antigens recognized and the SCFv clones employed 330. A polyclonal Tcm library comprised of approximately 5000 Tcm lines is stored as separate frozen stocks for each Tcm line using standard cryogenic methods for mammalian cells 340. Tcm lines expressing multi-specific CARs specific for currently identified human cell surface proteins, viral antigens, and other pathogens may be included in the library.

Example 4

Treatment of a Breast Cancer Patient with Multiple Tcm Lines Expressing Multi-Specific CARs A human subject that is a patient with breast cancer is treated with multiple Tcm lines which are selected based upon the gene expression profile of the patient's tumor cells. The patient's breast cancer tumor is surgically removed, and frozen sections are analyzed to obtain tumor cells for preparation of RNA. The identity of all genes expressed by the tumor cells (i.e., the transcriptome) is determined. Methods and instruments to isolate, amplify and determine the identity, i.e., nucleotide sequence, of all mRNAs expressed by a tumor cell, are identified (see e.g., Curtis et al., *Nature* 486: 346-352, 2012 and the Technical Bulletin: Whole-Genome Expression Analysis . . . available from Illumina, Inc., San Diego, Calif. which are incorporated herein by reference). The tumor cell transcriptome is analyzed to identify any expressed genes encoding cell surface proteins. Bioinformatics tools and methods to identify any of the approximately 3700 known human cell surface proteins which are expressed by the tumor cells are described (see e.g., Cunha et al., *Ibid.*).

Tcm lines expressing multi-specific CARs specific for cell surface antigens expressed by the patient's tumor cells are located from the searchable database and expanded. For example, a breast cancer tumor cell expressing the tumor associated antigens: HER-2/neu, MUC-1, and EGFR may be treated with three Tcm lines, expressing CAR specific for each of the surface antigens. Multi-specific CARs provide increased efficacy. For example, multi-specific antibodies have been developed for targeting cells expressing two antigens (see e.g., U.S. Pat. No. 5,601,819, and Phuphanich et al., *Cancer Immunol. Immunother.* 62: 125-135, 2013; each of which is incorporated herein by reference). Three Tcm lines expressing multi-specific CARs recognizing Her2 or MUC1 or EGFR are retrieved from the library and expanded in vitro to obtain approximately $10^9$ cells of each line. The patient is infused with approximately $10^7$ cells/kg of each Tcm line.

To treat metastatic cancer cells which may display a different set of cell surface antigens relative to the primary tumor, the transcriptome of metastatic tumor cells or circulating tumor cells may be determined. Tcm lines recognizing a new or altered set of surface antigens are selected from the library and administered to the patient. For example, metastatic breast cancer cells may lose expression of cell surface antigens (e.g., HLA-C) and gain expression of other antigens (e.g., CD51, integrin $\alpha_V$) (see e.g., Kischel et al., *Neoplasia* 10: 1014-1020, 2008 which is incorporated herein by reference. Methods to collect circulating tumor cells and harvest RNA for expression profiling are described (see e.g., Yu et al., *J. Cell Biol.* 192: 373-382, 2010 which is incorporated herein by reference). Tcm clones specific for the current set of surface antigens expressed by the metastatic tumor cells are selected from the Tcm library, expanded and administered to the patient.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal-bearing medium used to actually carry out the distribution. Examples of a signal-bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various embodiments described herein can be implemented, individually and/or collectively, by various types of electro-mechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electronics systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to implement devices and/or processes and/or systems in the fashion(s) set forth herein, and thereafter use engineering and/or business practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, hovercraft, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a voice-over IP system, etc.), (f) a business entity (e.g., an Internet Service Provider (ISP) entity such as Comcast Cable, Quest, Southwestern Bell, etc.), or (g) a wired/wireless services entity (e.g., such as Sprint, Cingular, Nextel, etc.), etc.

Those skilled in the art will appreciate that a user may be representative of a human user, a robotic user (e.g., computational entity), and/or substantially any combination thereof (e.g., a user may be assisted by one or more robotic). In addition, a user as set forth herein, although shown as a single entity may in fact be composed of two or more entities. Those skilled in the art will appreciate that, in general, the same may be said of "sender" and/or other entity-oriented terms as such terms are used herein.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

All publications, patents and patent applications cited herein are incorporated herein by reference. The foregoing specification has been described in relation to certain embodiments thereof, and many details have been set forth for purposes of illustration, however, it will be apparent to those skilled in the art that the invention is susceptible to additional embodiments and that certain of the details described herein may be varied considerably without departing from the basic principles of the invention.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for immunotherapy of a subject comprising: administering to a subject afflicted by or having symptoms of cancer, a therapeutically effective amount of one or more T cells bearing one or more multi-specific Chimeric Antigen Receptors including at least two antigen binding sites, wherein the multi-specific Chimeric Antigen Receptors have increased avidity or affinity for binding to at least two target antigens present on cancer cells compared to the avidity or affinity for binding the same target antigens also present on normal cells, wherein at least one of the target antigens includes at least one mutation in genetic sequence or difference in post-translational modification when expressed on cancer cells compared to when expressed on normal cells.

2. The method of claim 1, wherein the avidity or affinity of each multi-specific Chimeric Antigen Receptors is optimized to increase the specificity of the Chimeric Antigen Receptor for cancer cells, by selecting the avidity or affinity of each of the at least two antigen binding sites for their respective target antigens based on the cell surface antigen density or expression levels of at least two target antigens on cancer cells.

3. The method of claim 2, wherein the cell surface antigen density or expression level of a target antigen on cancer cells is higher compared with the antigen density or expression level of the same target antigen on normal cells.

4. The method of claim 1, wherein the one or more T cells bearing multi-specific Chimeric Antigen Receptors have been selected for the subject from a library of T cells bearing multi-specific Chimeric Antigen Receptors.

5. The method of claim 1, wherein the one or more T cells bearing multi-specific Chimeric Antigen Receptors recognize multiple epitopes of the same target antigen.

* * * * *

UNITED STATES PATENT AND TRADEMARK OFFICE

CERTIFICATE OF CORRECTION

PATENT NO. : 9,587,237 B2
APPLICATION NO. : 13/804224
DATED : March 7, 2017
INVENTOR(S) : Roderick A. Hyde et al.

It is certified that error appears in the above-identified patent and that said Letters Patent is hereby corrected as shown below:

In the Specification

Column 1, Line 41:
"Mar. 2013 with,"
Should read:
--Mar. 2013 with attorney docket no. 0412-004-001A-000000,--

Column 1, Line 47:
"Mar. 2013 with,"
Should read:
--Mar. 2013 With attorney docket no. 0412-004-001B-000000,--

In the Claims

Column 36, Line 14, Claim 2:
"of each multi-specific Chimeric Antigen Receptors"
Should read:
--of each multi-specific Chimeric Antigen Receptor--

Signed and Sealed this
Twenty-seventh Day of June, 2017

Joseph Matal

Joseph Matal
*Performing the Functions and Duties of the Under Secretary of Commerce for Intellectual Property and Director of the United States Patent and Trademark Office*